(12) United States Patent
Boden, Jr. et al.

(10) Patent No.: US 10,994,108 B2
(45) Date of Patent: May 4, 2021

(54) PROGRAMMABLE DRAINAGE VALVE WITH FIXED REFERENCE MAGNET FOR DETERMINING DIRECTION OF FLOW OPERABLE WITH ANALOG OR DIGITAL COMPASS TOOLSETS

(71) Applicant: Integra LifeSciences Switzerland Sárl, Le Locle (CH)

(72) Inventors: Thomas Boden, Jr., Middleboro, MA (US); Patricia D'Aoust, Franklin, MA (US); Alexander Arazawa, Cambridge, MA (US)

(73) Assignee: Integra LifeSciences Switzerland Sárl, Le Locle (CH)

( * ) Notice: Subject to any disclaimer, the term of this patent is extended or adjusted under 35 U.S.C. 154(b) by 741 days.

(21) Appl. No.: 15/708,496

(22) Filed: Sep. 19, 2017

(65) Prior Publication Data

US 2019/0083763 A1    Mar. 21, 2019

(51) Int. Cl.
*A61M 27/00*      (2006.01)
*G01R 33/00*      (2006.01)

(52) U.S. Cl.
CPC ....... *A61M 27/006* (2013.01); *G01R 33/0076* (2013.01); *A61M 2205/3317* (2013.01);
(Continued)

(58) Field of Classification Search
CPC .......... A61M 27/006; A61M 2205/103; A61M 2205/3317; A61M 2205/3331;
(Continued)

(56) References Cited

U.S. PATENT DOCUMENTS 3,902,252 A    9/1975    Farber
4,173,228 A    11/1979    Van Steenwyk et al.
(Continued)

FOREIGN PATENT DOCUMENTS

EP      2 826 517      1/2015

OTHER PUBLICATIONS

Copending, co-owned U.S. Appl. No. 15/708,404, filed Sep. 19, 2017.
(Continued)

*Primary Examiner* — Benjamin J Klein
(74) *Attorney, Agent, or Firm* — Cohen & Hildebrand, PLLC

(57) ABSTRACT

A method for using an implantable programmable bodily fluid drainage valve including a fixed reference magnet and an adjustable valve unit having a pair of primary magnetic elements. In accordance with the present inventive method the implantable programmable bodily fluid drainage valve is operable using either an intended toolset including a sensor array for detecting a magnetic field or a non-intended toolset employing an analog type compass assembly instead of the sensor array, wherein a location of the fixed reference magnet in the implantable programmable bodily fluid drainage valve and size of the fixed reference magnet has substantially no negative influence on operation of the analog type compass assembly of the non-intended toolset when used to operate the implantable programmable bodily fluid drainage valve.

5 Claims, 29 Drawing Sheets

(52) U.S. Cl.
CPC . *A61M 2205/3334* (2013.01); *A61M 2205/50* (2013.01); *A61M 2205/502* (2013.01); *A61M 2205/583* (2013.01); *A61M 2205/8206* (2013.01)

(58) Field of Classification Search
CPC ...... A61M 2205/3515; A61M 2205/50; A61M 2205/583; A61M 2205/6054; A61M 2205/70; G01R 33/005; G01R 33/0076
See application file for complete search history.

(56) References Cited

U.S. PATENT DOCUMENTS

| | | | |
|---|---|---|---|
| 4,595,390 A | 6/1986 | Hakim et al. | |
| 4,608,992 A | 9/1986 | Hakim et al. | |
| 4,622,644 A | 11/1986 | Hansen | |
| 4,839,809 A | 6/1989 | Leighton et al. | |
| 5,309,096 A | 5/1994 | Hoegnelid | |
| 5,425,382 A | 6/1995 | Golden et al. | |
| 5,438,990 A | 8/1995 | Wahlstrand et al. | |
| 5,525,901 A | 6/1996 | Clymer et al. | |
| 5,643,194 A | 7/1997 | Negre | |
| 5,709,225 A | 1/1998 | Budgifvars et al. | |
| 5,758,667 A | 6/1998 | Slettenmark | |
| 5,879,297 A | 3/1999 | Haynor et al. | |
| 6,101,417 A | 8/2000 | Vogel et al. | |
| 6,129,668 A | 10/2000 | Haynor et al. | |
| 6,138,681 A | 10/2000 | Chen et al. | |
| 6,216,028 B1 | 4/2001 | Haynor et al. | |
| 6,242,907 B1 | 6/2001 | Clymer et al. | |
| 6,263,230 B1 | 7/2001 | Haynor et al. | |
| 6,439,538 B1 | 8/2002 | Ito | |
| 6,485,449 B2 | 11/2002 | Ito | |
| 6,690,159 B2 | 2/2004 | Burreson et al. | |
| 6,702,249 B2 | 3/2004 | Ito | |
| 6,707,293 B2 | 3/2004 | Wan et al. | |
| 6,850,803 B1 | 2/2005 | Jimenez et al. | |
| 6,882,146 B2 | 4/2005 | Maiwald | |
| 6,883,241 B2 | 4/2005 | Moskowitz et al. | |
| 6,891,367 B2 | 5/2005 | Shinmura et al. | |
| 6,937,906 B2 | 8/2005 | Terry et al. | |
| 6,951,059 B2 | 10/2005 | Moskowitz et al. | |
| 7,126,331 B2 | 10/2006 | Johnson et al. | |
| 7,173,419 B1 | 2/2007 | Johnson et al. | |
| 7,228,252 B2 | 6/2007 | Alexander et al. | |
| 7,301,332 B2 | 11/2007 | Govari et al. | |
| 7,334,582 B2 | 2/2008 | Bertrand et al. | |
| 7,525,309 B2 | 4/2009 | Sherman et al. | |
| 7,753,913 B2 | 7/2010 | Szakelyhidi, Jr. et al. | |
| 7,842,004 B2 | 11/2010 | Kassem | |
| 7,856,987 B2 | 12/2010 | Bertrand et al. | |
| 7,921,571 B2 | 4/2011 | Moureaux et al. | |
| 7,945,334 B2 | 5/2011 | Jimenez et al. | |
| 8,015,977 B2 | 9/2011 | Bertrand et al. | |
| 8,038,641 B2 | 10/2011 | Soares et al. | |
| 8,148,978 B2 | 4/2012 | Sherman et al. | |
| 8,241,240 B2 | 8/2012 | Murphy | |
| 8,257,296 B2 | 9/2012 | Bertrand et al. | |
| 8,322,365 B2 | 12/2012 | Wilson et al. | |
| 8,398,617 B2 | 3/2013 | Ginggen et al. | |
| 8,518,023 B2 | 8/2013 | Roth et al. | |
| 8,539,956 B2 | 9/2013 | Bertrand et al. | |
| 8,591,499 B2 | 11/2013 | Girardin et al. | |
| 8,617,142 B2 | 12/2013 | Wilson et al. | |
| 8,622,978 B2 | 1/2014 | Bertrand et al. | |
| 8,630,695 B2 | 1/2014 | Negre et al. | |
| 8,733,394 B2 | 5/2014 | Negre et al. | |
| 8,753,331 B2 | 6/2014 | Murphy | |
| 8,862,200 B2 | 10/2014 | Sherman et al. | |
| 9,126,010 B2 | 9/2015 | Shah et al. | |
| 9,149,615 B2* | 10/2015 | Wilson | A61M 27/006 |
| 9,220,876 B2 | 12/2015 | Girardin et al. | |
| 9,242,077 B2 | 1/2016 | Wilson et al. | |
| 9,295,826 B2 | 3/2016 | Bertrand et al. | |
| 9,364,646 B2 | 6/2016 | Bertrand et al. | |
| 9,381,301 B2 | 7/2016 | Lattanzio et al. | |
| 9,427,559 B2 | 8/2016 | Shah et al. | |
| 9,453,934 B2 | 9/2016 | Hughes | |
| 9,585,600 B2 | 3/2017 | Sharonov | |
| 2004/0017192 A1 | 1/2004 | Clymer et al. | |
| 2004/0055610 A1 | 3/2004 | Forsell | |
| 2004/0064030 A1 | 4/2004 | Forsell | |
| 2004/0097803 A1 | 5/2004 | Panescu | |
| 2004/0250820 A1 | 12/2004 | Forsell | |
| 2005/0187509 A1 | 8/2005 | Wolf | |
| 2006/0124140 A1 | 6/2006 | Forsell | |
| 2007/0276218 A1 | 11/2007 | Yellen | |
| 2010/0010338 A1 | 1/2010 | van Dam et al. | |
| 2010/0292759 A1 | 11/2010 | Hahn et al. | |
| 2011/0031961 A1 | 2/2011 | Durand et al. | |
| 2012/0041297 A1 | 2/2012 | McGary | |
| 2012/0302938 A1 | 11/2012 | Browd et al. | |
| 2013/0197422 A1 | 8/2013 | Browd et al. | |
| 2014/0336560 A1 | 11/2014 | Hakim | |
| 2015/0196742 A1 | 7/2015 | Browd et al. | |
| 2016/0089519 A1 | 3/2016 | Bittenson | |
| 2016/0166813 A1 | 6/2016 | Bertrand et al. | |
| 2016/0184563 A1 | 6/2016 | Bertrand et al. | |
| 2016/0279396 A1 | 9/2016 | Bertrand et al. | |
| 2017/0095650 A1 | 4/2017 | Wilson | |
| 2017/0209056 A1 | 7/2017 | Browd et al. | |
| 2018/0001064 A1 | 1/2018 | Pfleiderer | |
| 2018/0015266 A1* | 1/2018 | Amery | H03F 1/52 |
| 2018/0126147 A1 | 5/2018 | Hakim | |
| 2018/0184943 A1 | 7/2018 | Boden | |
| 2018/0243542 A1 | 8/2018 | Pfleiderer et al. | |

OTHER PUBLICATIONS

Copending, co-owned U.S. Appl. No. 15/708,549, filed Sep. 19, 2017.

Copending, co-owned U.S. Appl. No. 15/708,600, filed Sep. 19, 2017.

* cited by examiner

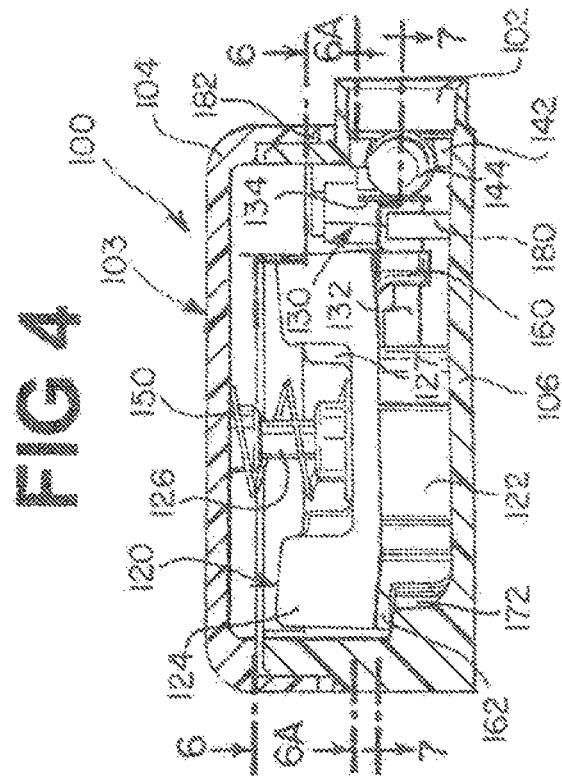

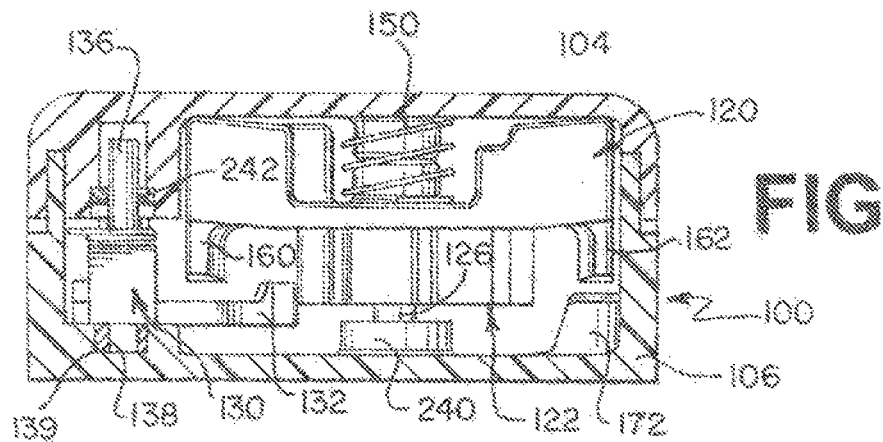
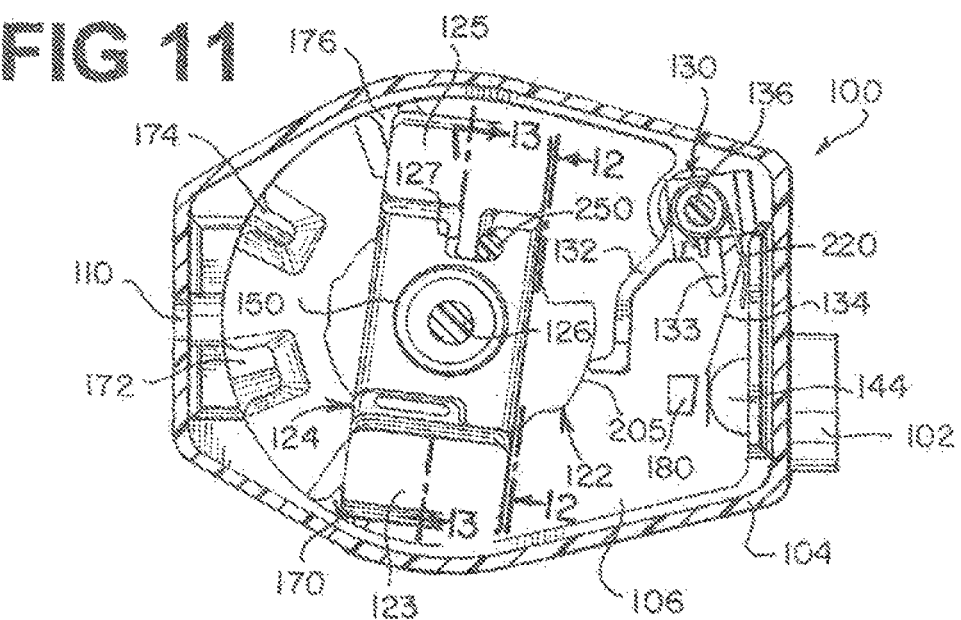
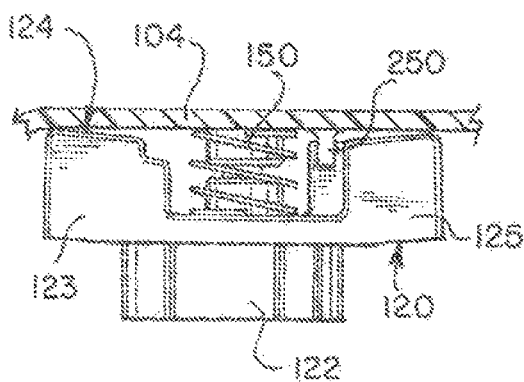

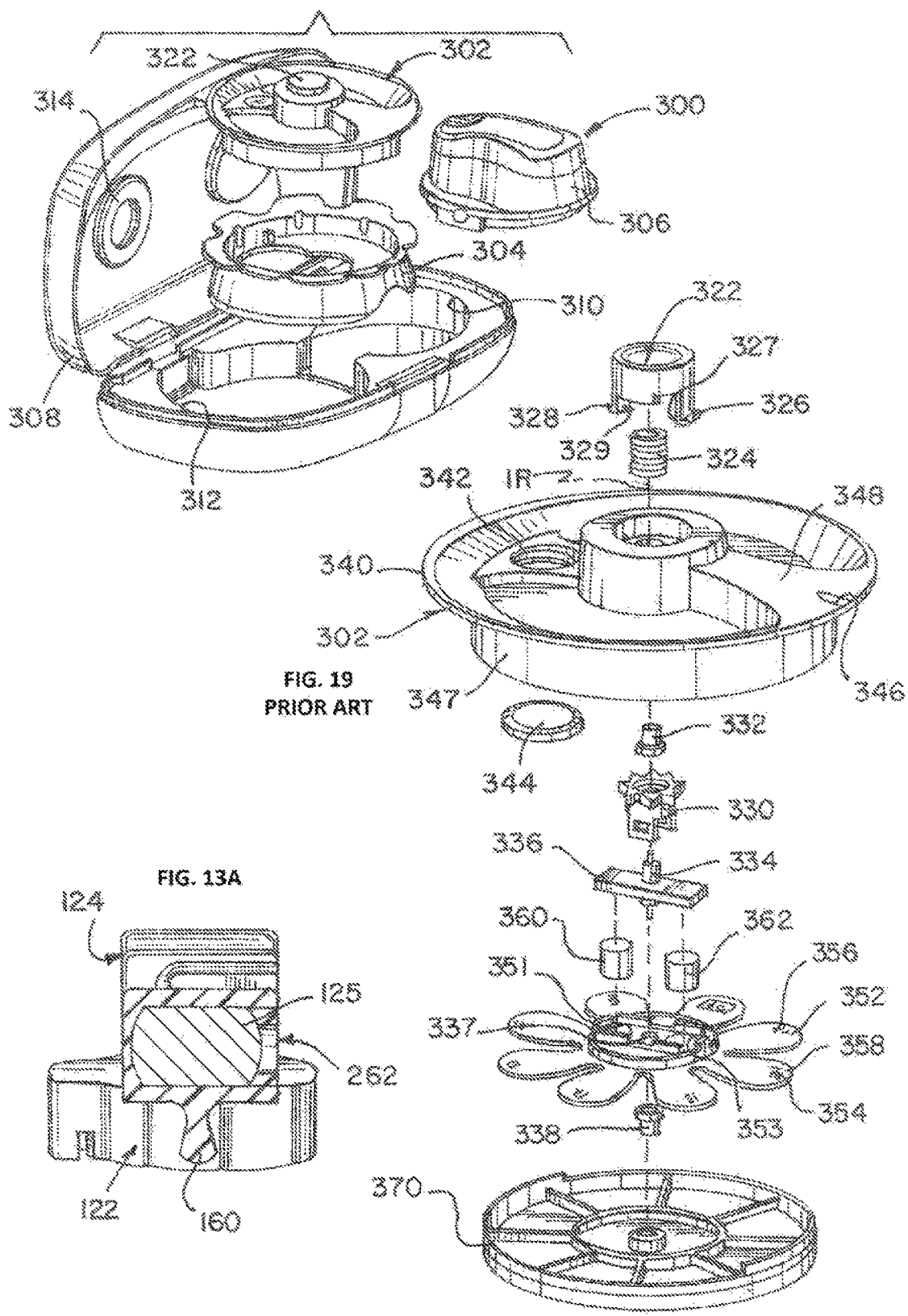

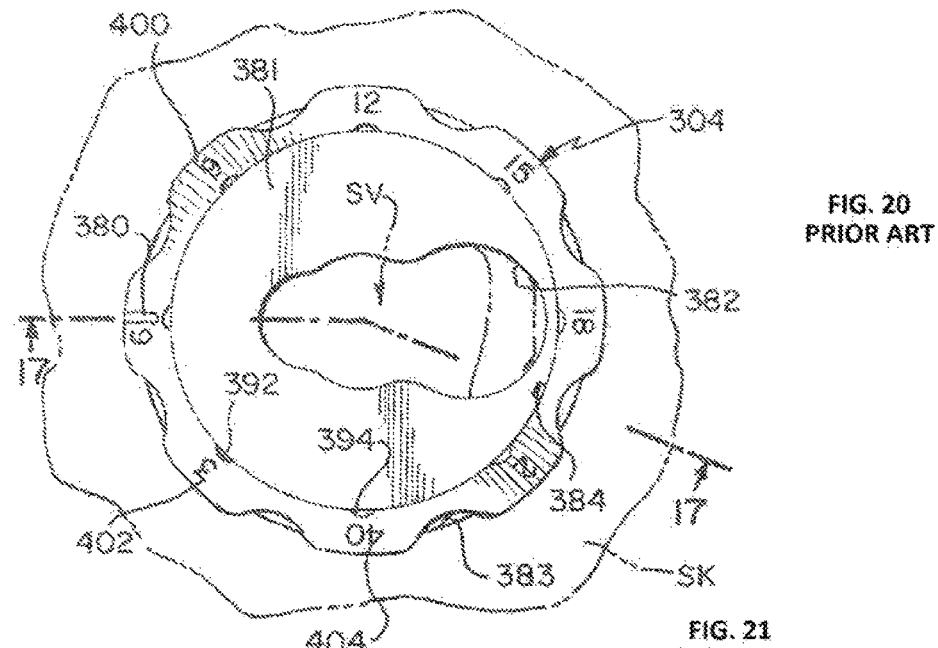
FIG. 20
PRIOR ART
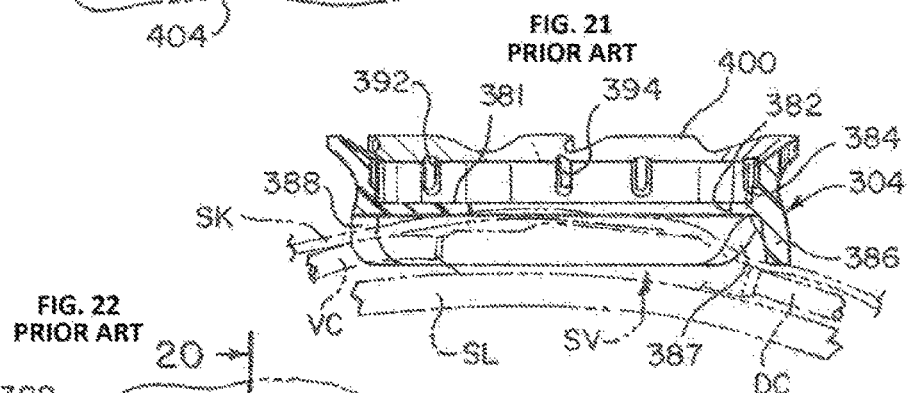
FIG. 21
PRIOR ART
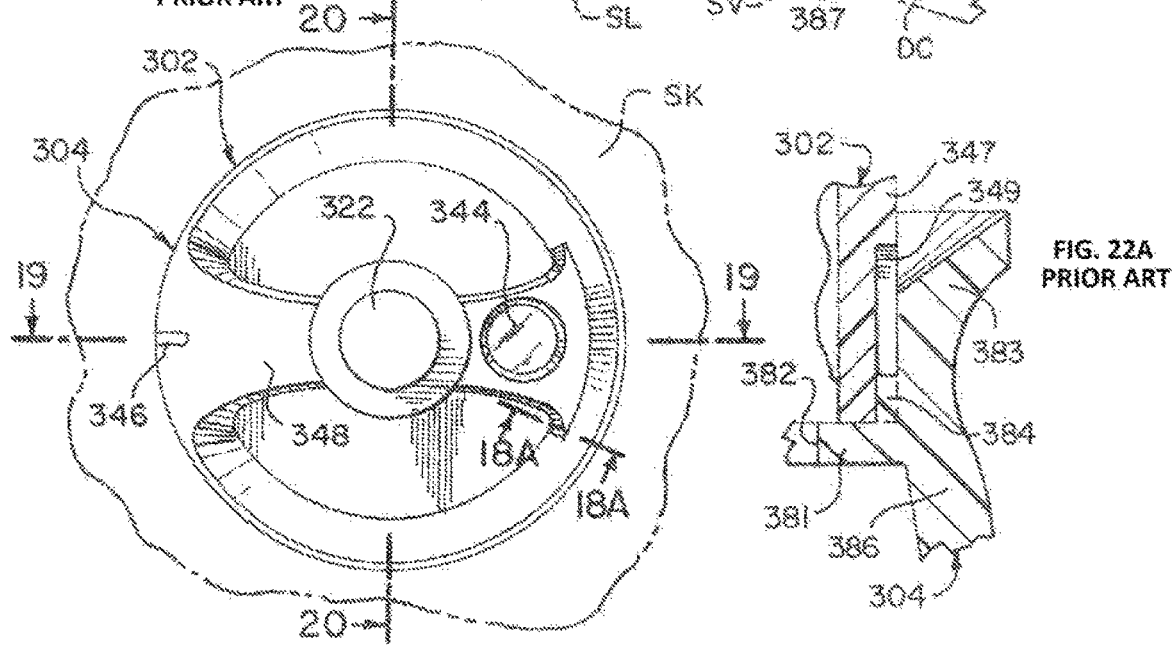
FIG. 22
PRIOR ART
FIG. 22A
PRIOR ART

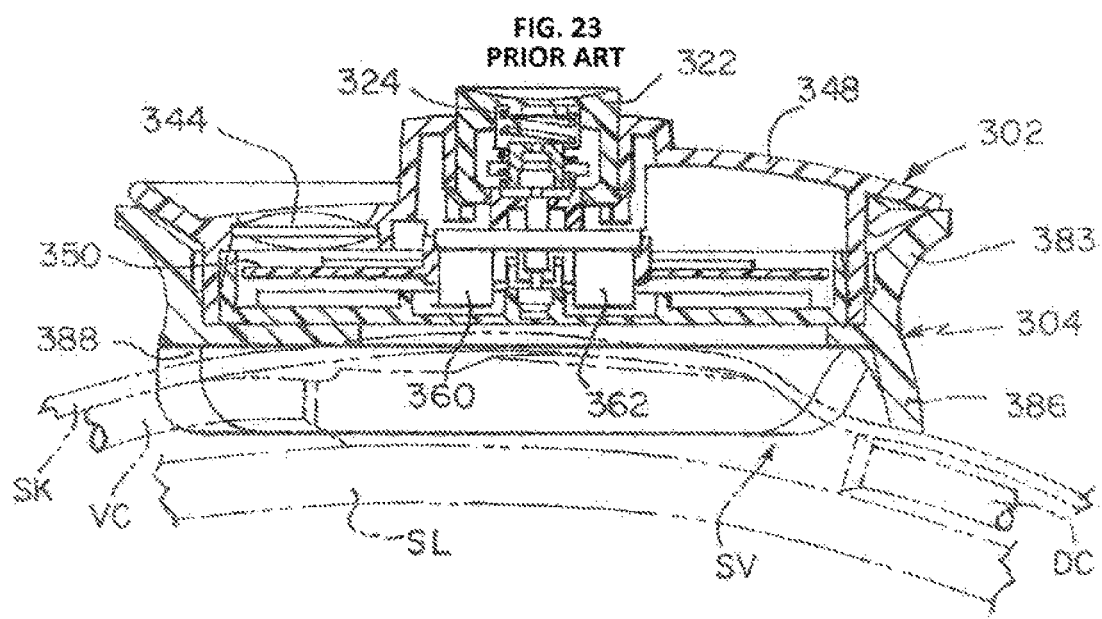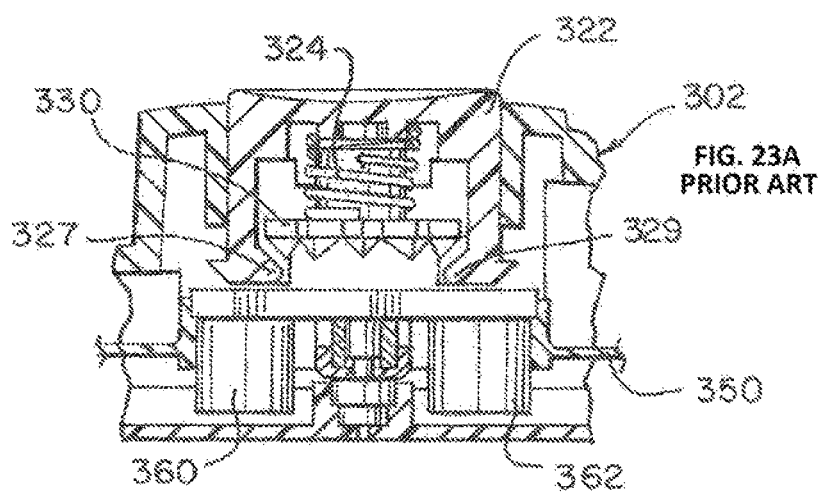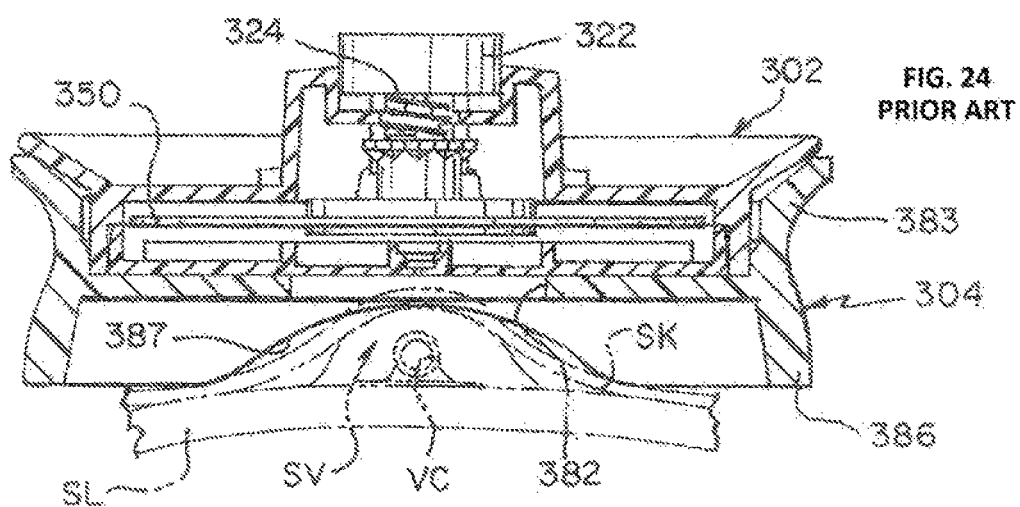

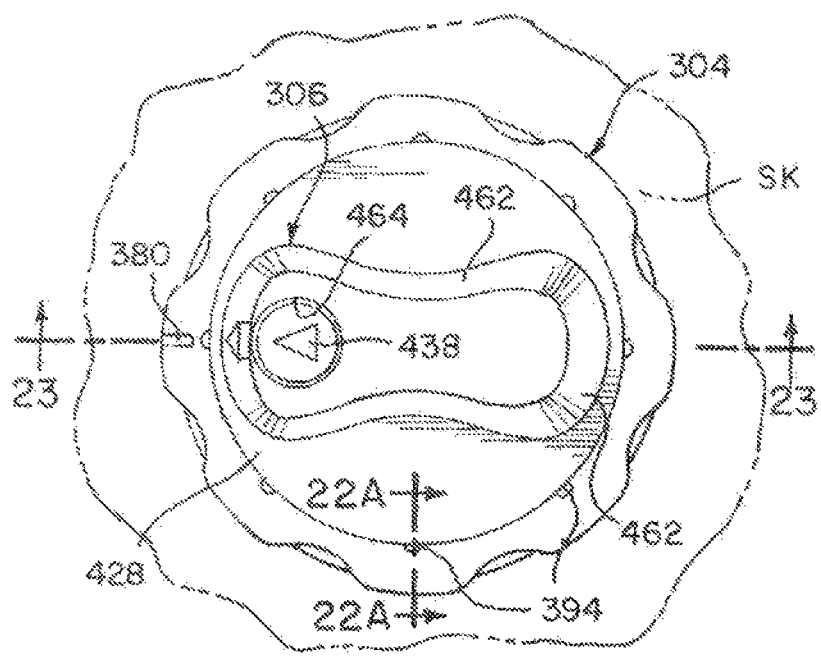
FIG. 26
PRIOR ART
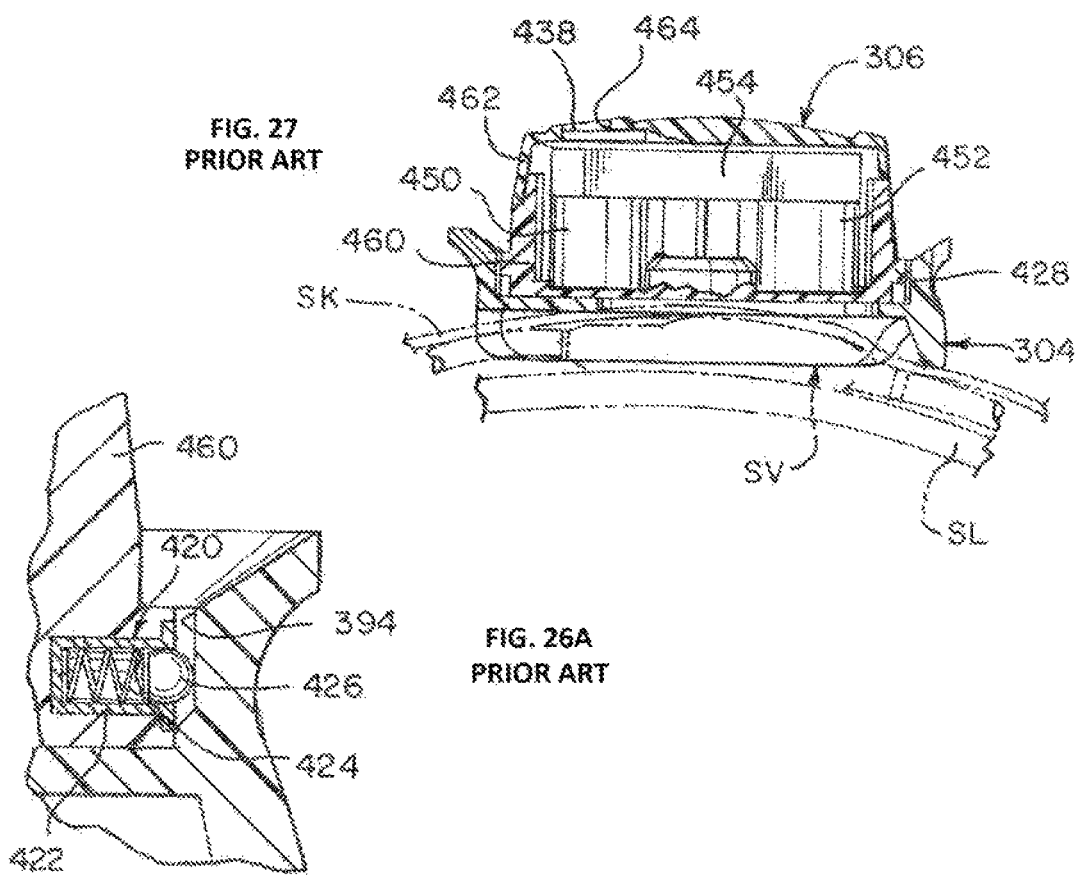
FIG. 27
PRIOR ART
FIG. 26A
PRIOR ART

PROGRAMMABLE DRAINAGE VALVE WITH FIXED REFERENCE MAGNET FOR DETERMINING DIRECTION OF FLOW OPERABLE WITH ANALOG OR DIGITAL COMPASS TOOLSETS

BACKGROUND OF THE INVENTION

Field of the Invention

The present invention relates to a system and method for use of an implantable drainage valve for drainage of a bodily fluid (e.g., cerebrospinal fluid). In particular, the present inventive system and method is directed to a drainage valve that includes a fixed reference magnet for determining the implant's angle of orientation (i.e., direction of flow) operable using either an analog or digital compass indicator of an electronic toolset.

Description of Related Art

Hydrocephalus is the accumulation of cerebrospinal fluid in the brain, resulting from increased production, or more commonly, pathway obstruction or decreased absorption of the fluid. Cerebrospinal fluid (CSF) shunts have been used for decades for the treatment of hydrocephalus. A CSF shunt involves establishing an accessory pathway for the movement of CSF to bypass an obstruction of the natural pathways.

The shunt is positioned to enable the CSF to be drained from the cerebral ventricles or sub-arachnoid spaces into another absorption site (e.g., the right atrium of the heart or the peritoneal cavity) through a system of small catheters. A regulatory device, such as a valve, may be inserted into the pathway of the catheters. In general, the valve keeps the CSF flowing away from the brain and moderates the pressure or flow rate. The drainage system using catheters and valves enables the excess CSF within the brain to be evacuated and, thereby, the pressure within the cranium to be reduced.

Some implantable valves are fixed pressure valves (i.e., monopressure valves) while others have adjustable or programmable settings. Programmable or adjustable implantable valves are desirable in that the valve pressure setting may be varied non-invasively via an external control device over the course of treatment without requiring explantation. One such conventional adjustable or programmable implantable valve using magnets is the CODMAN® HAKIM® Programmable Valve (CHPV), as disclosed in U.S. Pat. No. 4,595,390, which is assigned to DePuy Orthopedics, a J&J company related to that of the present assignee, and herein incorporated by reference in its entirety. Another programmable implantable drainage valve is the CODMAN® CERTAS® or CERTAS® Plus Programmable Valve, as disclosed in U.S. Pat. No. 8,322,365, also assigned to DePuy Orthopedics, a J&J company related to that of the present assignee, and which is herein incorporated by reference in its entirety. Medtronic also has a programmable implantable shunt valve Strata® controlled using magnets. Still other prior art programmable valves include Miethke BBraun ProGav2.0 and Sophysa Polaris. The pressure setting in any of these aforementioned conventional programmable implantable valves may be non-invasively adjusted post implantation in the body using a rotating construct or rotor with a pair of magnets.

Each programmable implantable valve is controlled using an associated toolset comprising one or more devices used to locate the valve, read the current valve indication and adjust the valve to a new setting. Heretofore, each version or generation of programmable valve was to be used only with its corresponding version or generation of toolset. To select the appropriate generation or version of toolset, required that the user first identify which version or generation of the programmable valve was implanted prior to selecting the corresponding version or generation of toolset. This may be accomplished via X-ray imaging (e.g., identifying the presence or absence of a reference magnet), however, such exposure has deleterious health effects and thus is to be avoided whenever possible. Another drawback is that medical facilities would require an allocation of space for storing of the different versions or generations of electronic toolsets. However, by far one of the most relevant risks is the possible selection and use by medical personnel of an incompatible generation or versions of toolset with the implanted valve. While still another factor is the familiarity and experience that medical personnel may have with using a different toolset.

These risks and drawbacks are reduced or overcome by developing an improved programmable valve that remains compatible with a version or generation of toolset other than the one intended. That is, to develop an improved programmable valve including at least one fixed reference magnet for determining the angle of orientation (i.e., the direction of flow) of the programmable valve, wherein the programmable valve is operable with its intended toolset (i.e., a toolset including an indicator tool that determines the orientation via electronic feedback from a sensor array to individually differentiate the fixed reference magnet (hereinafter referred to as a "digital compass")) while still remaining compatible with a non-intended toolset (i.e., a toolset including an indicator tool that is incapable of differentiating the fixed reference magnet and relies exclusively on manual physical palpation to determine the orientation (hereinafter referred to as an "analog compass").

SUMMARY OF THE INVENTION

An aspect of the present invention is directed to an improved programmable valve that remains compatible with a version or generation of toolset other than the one intended. That is, an improved programmable valve including at least one fixed reference magnet for determining the angle of orientation (i.e., the direction of flow) of the programmable valve, wherein the programmable valve is operable with its intended toolset (i.e., a toolset including an indicator tool that determines the orientation via electronic feedback from a sensor array to individually differentiate the fixed reference magnet (hereinafter referred to as a "digital compass")) while still remaining compatible with a non-intended toolset (i.e., a toolset including an indicator tool that is incapable of differentiating the fixed reference magnet and relies exclusively on manual physical palpation to determine the orientation (hereinafter referred to as an "analog compass").

Another aspect of the present invention relates to a method for using an implantable programmable bodily fluid drainage valve including a fixed reference magnet and an adjustable valve unit having a pair of primary magnetic elements. In accordance with the present inventive method the implantable programmable bodily fluid drainage valve is operable using either an intended toolset including a sensor array for detecting a magnetic field or a non-intended toolset employing an analog type compass assembly instead of the sensor array, wherein a location of the fixed reference magnet in the implantable programmable bodily fluid drainage valve and size of the fixed reference magnet has substantially no negative influence on operation of the analog type compass assembly of the non-intended toolset when used to operate the implantable programmable bodily fluid drainage valve.

BRIEF DESCRIPTION OF THE DRAWING

The foregoing and other features of the present invention will be more readily apparent from the following detailed description and drawings of illustrative of the invention wherein like reference numbers refer to similar elements throughout the several views and in which:

FIG. 3 is a top view of the adjustable valve unit of FIG. 2;

FIG. 4 is a side cross-sectional view of the adjustable valve unit of FIG. 3 along lines 4-4;

FIG. 10 is a side cross-sectional view of the adjustable valve unit of FIG. 8 along lines 10-10 showing axial lifting of the rotatable construct;

FIG. 11 is a shallower partial top cross-sectional view of the adjustable valve unit of FIG. 6H showing the "virtual off" position in an unconstrained condition;

FIG. 12 is a side view along lines 12-12 of FIG. 11;

FIG. 13A is a partial cross-sectional view along lines 13A-13A of FIG. 13;

FIG. 18 is a perspective view of a prior art toolset including an indicator tool, a locator tool, and a setting adjuster tool;

FIG. 19 is an exploded perspective view of the indicator tool of FIG. 18;

FIG. 20 is a top plan view of the locator tool of FIG. 18 positioned over an implanted valve;

FIG. 21 is a side cross-sectional view along lines 17-17 of FIG. 20, showing in phantom the shunt valve implanted under the skin in a patient;

FIG. 22 is a top plan view of the indicator tool nested with the locator tool;

FIG. 22A is a side cross-sectional view along lines 18A-18A of FIG. 22;

FIG. 23 is a side cross-sectional view along lines 19-19 of FIG. 22 with a release button in a normal, engaged position;

FIG. 23A is a partial side cross-sectional view along lines 19-19 of FIG. 22 showing the release button in a depressed, disengaged position;

FIG. 24 is a partial cross-sectional view along lines 20-20 of FIG. 22;

FIG. 26 is a top plan view of the adjuster tool nested with the locator tool;

FIG. 26A is a partial cross-sectional view along lines 22A-22A of FIG. 26;

FIG. 27 is a partial cross-sectional view along lines 23-23 of FIG. 26;

DETAILED DESCRIPTION OF THE INVENTION

Figure 1:
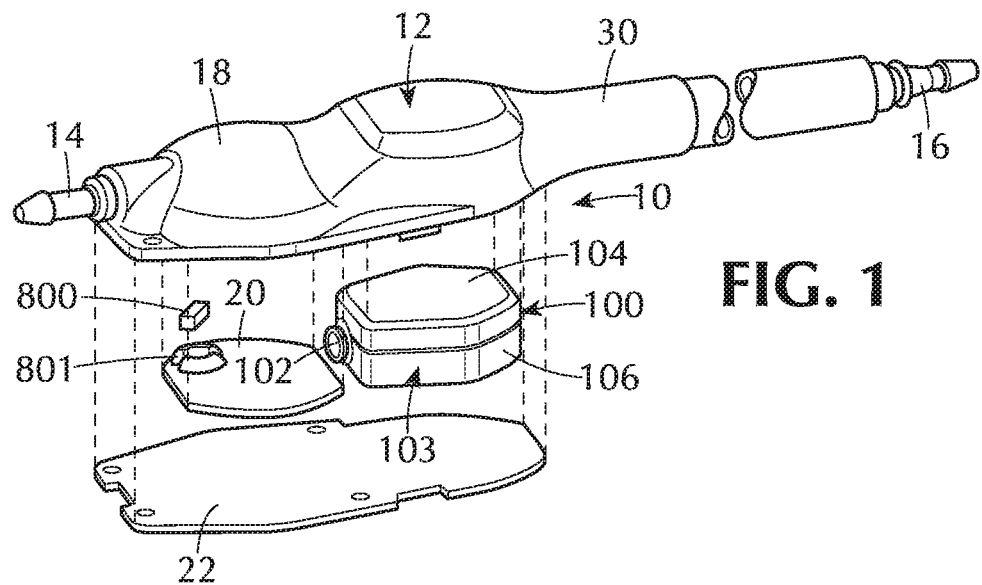
FIG. 1 is a schematic perspective exploded view of a programmable implantable valve device having a fixed reference magnet in addition to the rotational primary magnetic elements associated with the adjustable valve unit.

FIG. 1 illustrates a programmable shunt valve device 10 having a shunt housing 12, preferably formed of a translucent material such as silicone, with proximal connector 14 and distal connector 16. A ventricular catheter or other proximal catheter is connectable to connector 14 to bring fluid into shunt housing 12. Fluid passes into sampling or pumping chamber 18 and then through a valve mechanism in inlet 102 into adjustable valve unit 100, which is shown and described in more detail below in relation to FIGS. 2-13A. Adjustable valve unit 100, FIG. 1, includes a casing 103 formed as upper casing 104 and lower casing 106 which are joined by sonic welding in this construction. A needle guard 20, preferably formed of a rigid polymeric material, and lower casing 106 are secured within housing 12 by a backing plate 22, preferably formed of silicone reinforced with a polymeric mesh, which is bonded to housing 12 by a medical grade epoxy. A fixed reference magnet 800, as described in detail further below, is preferably seated in a bump or projection 801 on the needle guard 20.

When fluid pressure at inlet 102 exceeds a selected pressure setting within adjustable valve unit 100, fluid is admitted past a valve mechanism and then flows through valve unit outlet 110 into passage 30 of housing 12. Ultimately, fluid exits from housing 12 through distal connector 16 into a peritoneal catheter or other distal catheter.

Figure 2:
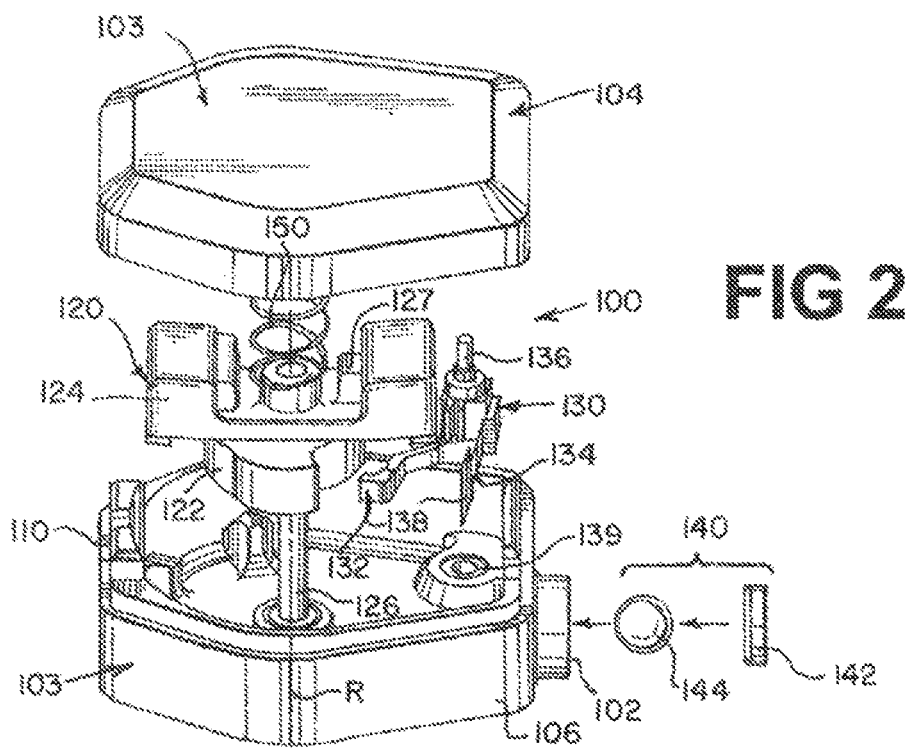
FIG. 2 is an exploded perspective view of the adjustable valve unit of FIG. 1.

Adjustable valve unit 100, FIG. 2, includes a rotor 120, spring arm unit 130, valve mechanism 140, and a rotor retention spring 150. Rotor 120, also referred to as a rotating construct, is formed of a lower cam structure 122 having a plurality of radially flat cam surfaces, as shown and described in more detail below, and an upper, magnet housing 124 carrying magnetic elements 123 and 125, N and S pole magnets, respectively. Housing 124 also defines a finger 127 which engages a stop in upper casing 104 when rotor 120 is moved to an unconstrained condition as described below. Rotor 120 rotates about axle 126 which defines a substantially fixed axis of rotation R at a first location in casing 103.

Preferably, rotor 120 is also capable of moving along the axis of rotation, in a translational motion, to an unconstrained condition when an adjustment tool from an electronic toolset is applied to it, as described in more detail below. Retention spring 150 biases rotor 120 to a downward, normally constrained condition. Preferably, spring 150 is a coil spring having sufficient bias to resist the effect of gravity, regardless of the position of the adjustable valve unit 100, and to resist magnetic or ferrous objects, such as magnets in an integrated locator/indicator tool from the electronic toolset, as described in more detail below. However, spring 150 is insufficient to resist the effects of the adjustment tool, also described below. Lower cam section 122 has a sufficient height to ensure that cam follower 132 remains in contact with a cam surface in both the constrained and unconstrained conditions.

Spring arm unit 130 includes cam follower 132, a resilient spring element 134 as well as upper and lower axles 136, 138 at a second location in casing 103. Axle 138 turns about a bearing 139 formed of a relatively low-friction, relatively hard material such as synthetic ruby. It is desirable for casing 103, rotor 120 and spring arm unit 130 to be formed of polyether sulfone, while all spring components are formed of medical grade non-ferromagnetic stainless steel.

Valve mechanism 140 includes seat 142 and movable valve member 144. Preferably, seat 142 and valve member 144, such as a ball, are formed of the same non-ferromagnetic material such as synthetic ruby. In other constructions, the movable valve member 144 may be a disc, a cone, or other type of plug. A spherical ball is currently preferred as the moveable valve member because that shape enables tight, precise tolerances, assembly and control relative to the valve seat. Also, the position of the seat within a port can be adjusted during assembly of the valve unit to alter the actual performance value achieved at each setting, using a force versus displacement relationship. First, a mandrel checks the position of the ball, and the seat is inserted to an estimated desirable location within the port. Ball displacement is tested at one or more settings to confirm that desired performance will be achieved.

Figure 4A:
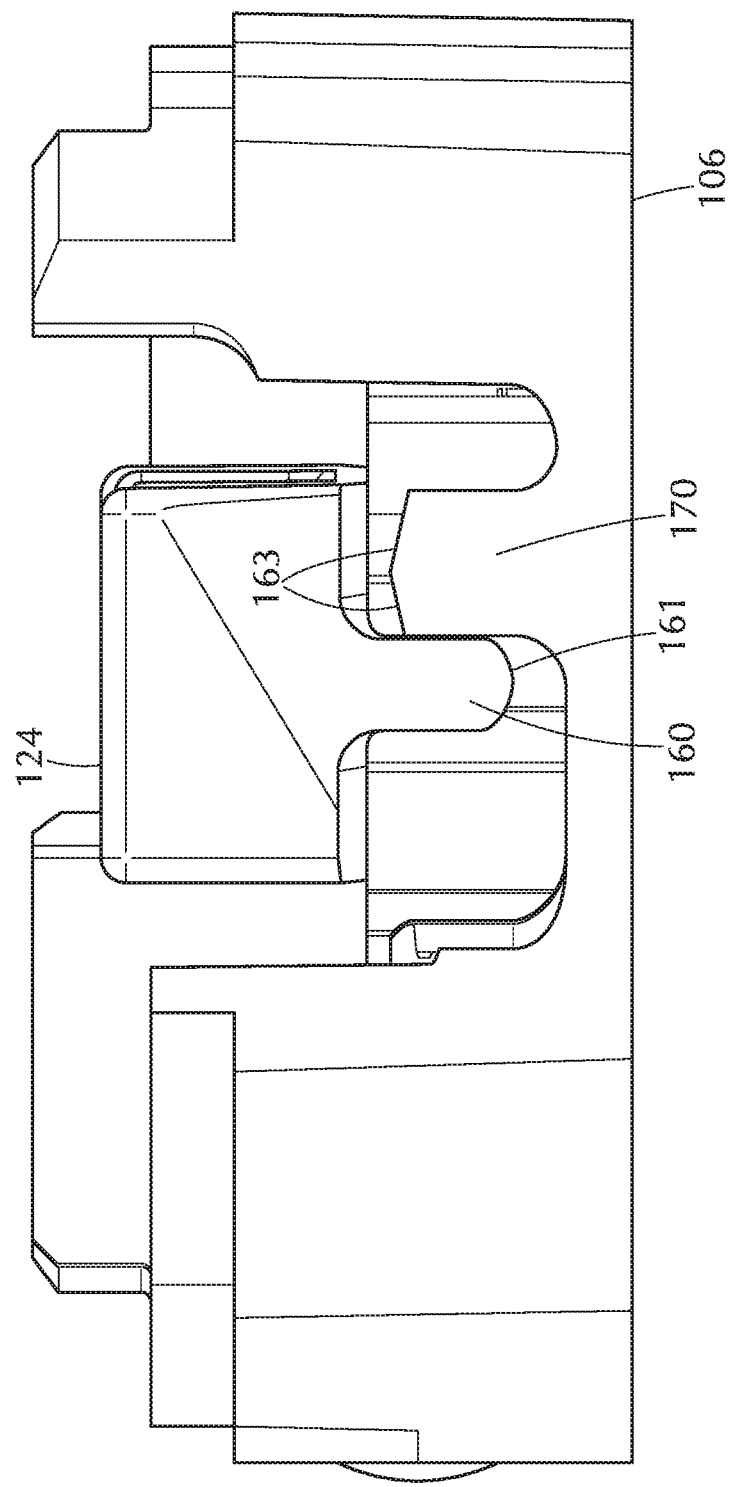
FIG. 4A is a side view of a single rotor tooth in engagement with a single lock stop.
Figure 5:
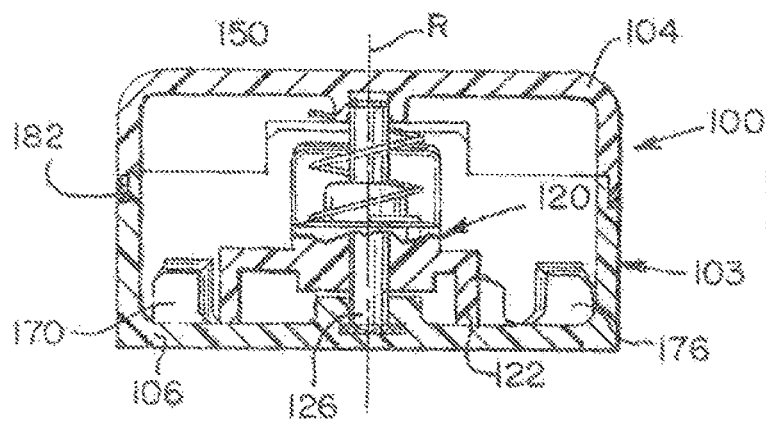
FIG. 5 is a cross-sectional view of the adjustable valve unit of FIG. 3 along lines 5-5.

Adjustable valve unit 100 is shown assembled in FIGS. 3-5 and positioned at a second pressure setting, as described in more detail below. Rotor housing 124 carries downwardly projecting teeth 160 and 162 with cooperate with four lock stops 170, 172, 174, 176 projecting upwardly from lower casing 106 in this construction. Lock stop 172 is shown in partial cross-section in FIG. 4 and lock stops 170 and 176 are visible in FIG. 5. Preferably, the lower surfaces 161 of rotor teeth 160 and 162 are rounded and the upper surfaces of casing lock stops 170, 172, 174 and 176 each have a plurality of facets 163 to create a chisel-like, lead-in topography which encourages the rotor teeth to return to a constrained position, as illustrated in the side view in FIG. 4A. However, the vertical surfaces of the rotor teeth 160, 162 and of lock stops 170-176 abut when engaged and do not "lead out", that is, relative translational movement is discouraged, once again illustrated in FIG. 4A. Pure vertical lift must therefore be provided by an adjustment tool, as described in more detail below, to overcome the rotor teeth-to-lock stop abutment and change the performance setting.

A limiter 180, FIG. 4, restricts travel of spring 134 away from seat 142 so that ball 144 does not become misaligned or dislodged relative to seat 142. A gasket 182 of epoxy is shown in FIGS. 4 & 5 as an optional, redundant seal between upper casing 104 and lower casing 106 in this construction.

Figure 6:
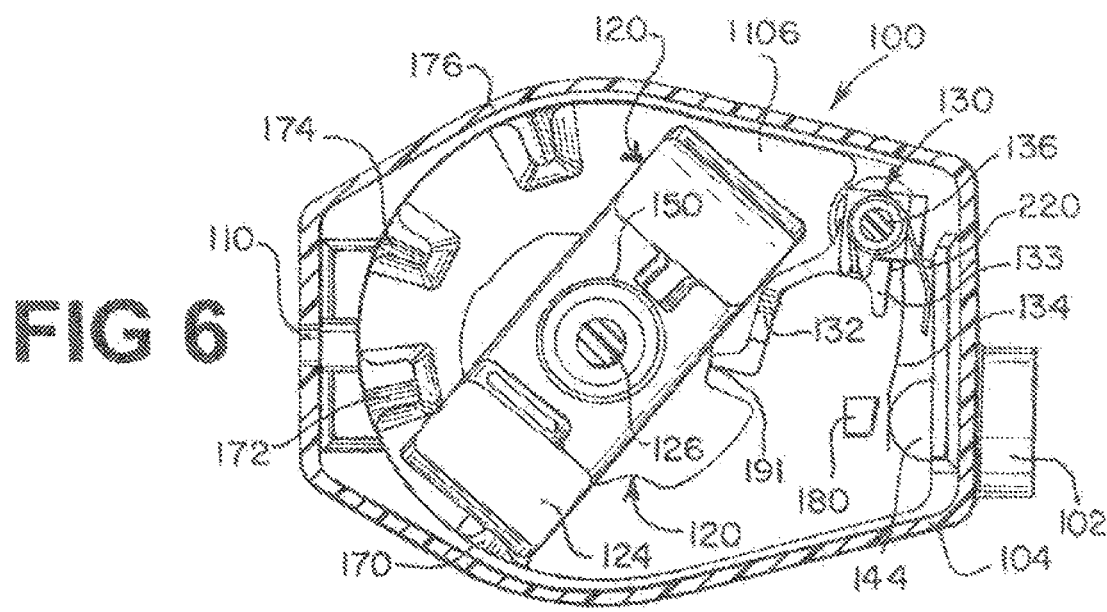
FIG. 6 is a partial cross-sectional view of the adjustable valve unit of FIG. 4 approximately along lines 6-6 at a first pressure setting.
Figure 6A:
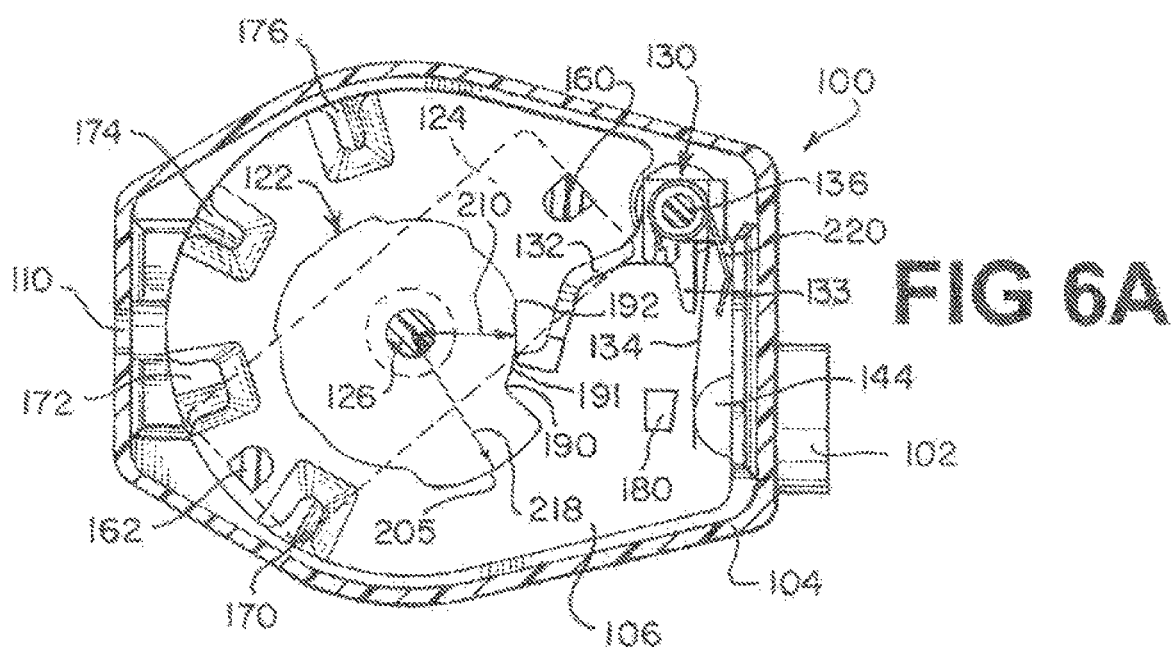
FIG. 6A is a deeper cross-sectional view of the adjustable valve unit of FIG. 4 approximately along lines 6A-6A at a first pressure setting.
Figure 7:
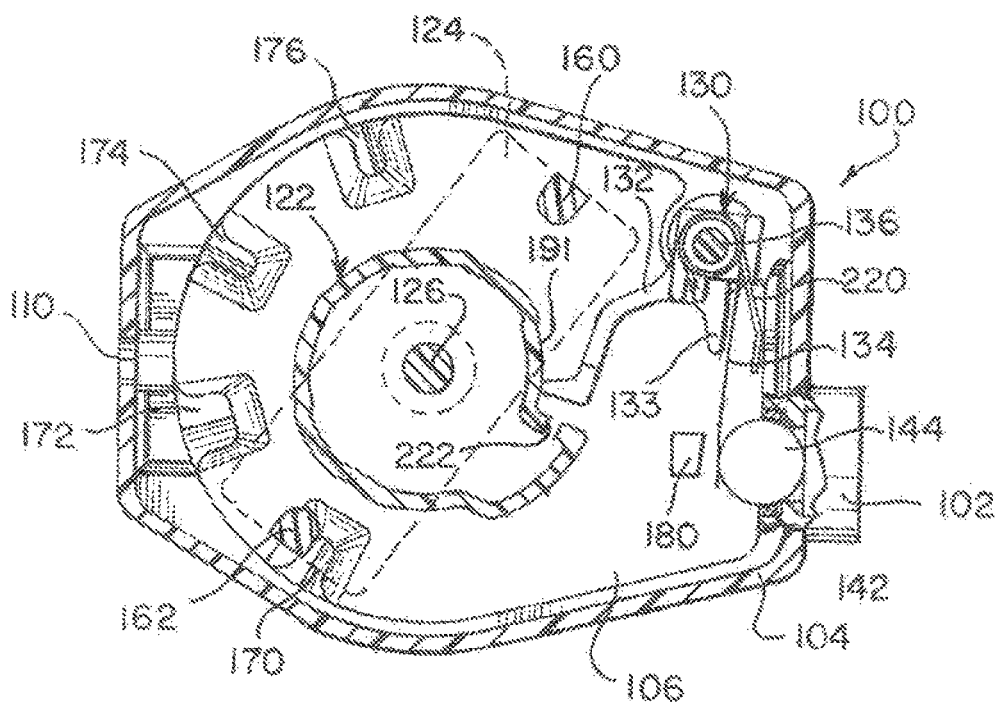
FIG. 7 is a deeper cross-sectional view of the adjustable valve unit of FIG. 4 along lines 7-7.
Figure 8:
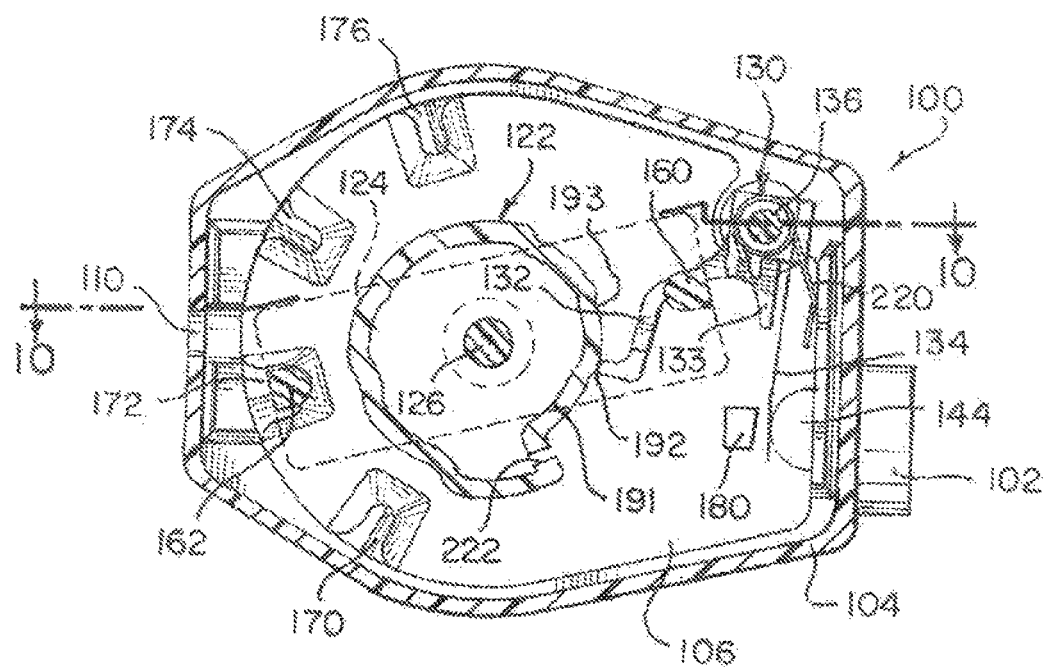
FIG. 8 is a cross-sectional view of the adjustable valve unit of FIG. 7 showing the transition to a different pressure setting.

The operation of adjustable valve unit 100 is illustrated in FIGS. 6-8 with identical reference numerals identifying identical components and features. Not all such components and features are labelled in each drawing for the sake of visual clarity. FIGS. 6 & 6A show different levels of top partial cross-sectional views for adjustable valve unit 100 at a first pressure setting. Cam follower 132 slidably contacts only a first cam surface 191, which has an arc length bounded by points 190 and 192, because rotor housing tooth 162 is captured between casing lock stops 170 and 172 in the normal, constrained condition. First cam surface 191 has a first, preferably shortest radial distance 210 relative to the axis of rotation of rotor 120. By comparison, outermost cam surface 205 has a greatest radial distance 218. An optional torsion spring 220 is shown in greater detail in FIG. 9.

When rotor 120 is translated upwardly by magnets using an adjustment tool rotor tooth 162 is lifted so that subsequent clockwise or counter-clockwise rotation of the adjustment tool rotates rotor tooth 162 up and over casing lock stop 172. After the adjustment tool is removed and when the second pressure setting has been selected as shown in FIG. 6B, rotor 120 is biased downwardly by spring 150, FIGS. 2, 4 & 5.

Figure 6B:
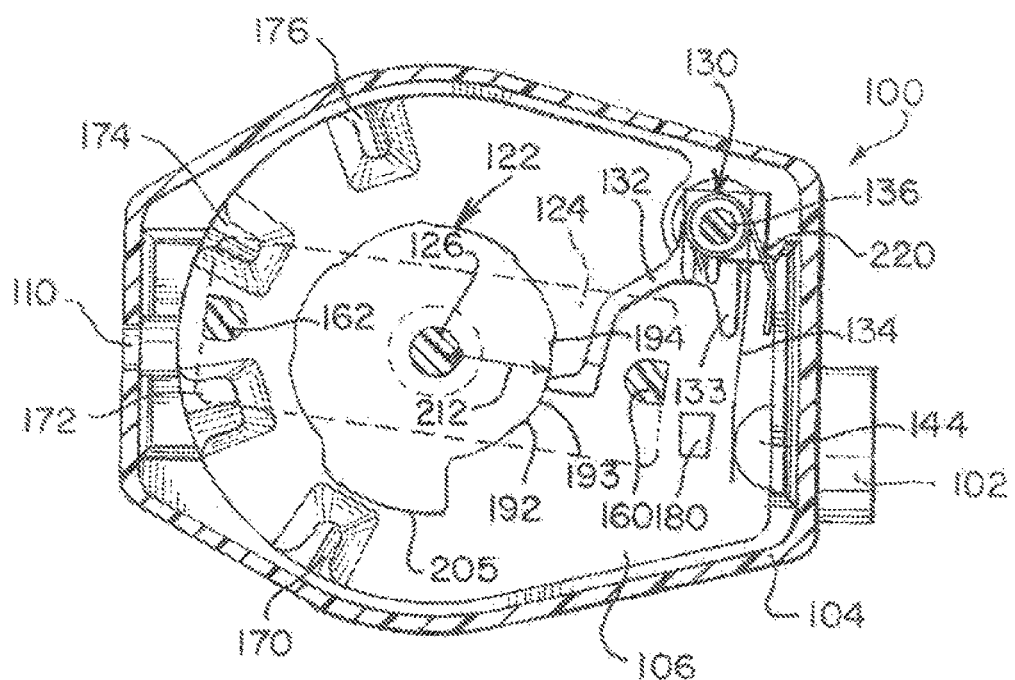
FIGS. 6B-6H are partial cross-sectional view of the adjustable valve unit of FIG. 4 at different, successive pressure settings.

Rotor tooth 160 is illustrated as not being in contact with any stop in FIGS. 4 & 6B, for example, because in the constrained condition rotor tooth 162 is now captured between a pair of adjacent lock stops 172 and 174, FIG. 6B, which is sufficient to prevent rotation of rotor 120 relative to the cam follower 132 beyond points 192 and 194 on the cam structure of rotor 120. Points 192 and 194 represent a second arc length for second cam surface 193. Surface 193 is at a second radial distance 212 which is greater than distance 210 and is less than distance 218, FIGS. 6A & 6H. The arc length of second cam surface 193, FIG. 6B, can be the same or different than the arc length of first cam surface 191 but, preferably, is substantially the same length.

The outward radial motion of cam follower 132 as it slidably travels from first cam surface 191, FIG. 6A, to second cam surface 193, FIG. 6B, increases the biasing force by valve spring 134 on ball 144 as increased torque is applied by cam follower 132 to the remainder of spring arm unit 130. Improved precision in pressure control is achieved by having a stiff cam follower 132 in contact with the selected cam surface and a flexible element, spring 134, in contact with the valve ball 144. The enhanced result is opening of the ball 144 from the valve seat 142 by requiring only the resilient spring element 134 to bend, which provides a constant spring force to the ball 144. The opening pressure, and overall valve performance, is not reliant on axial pivoting of the spring arm unit 130.

Figure 6C:
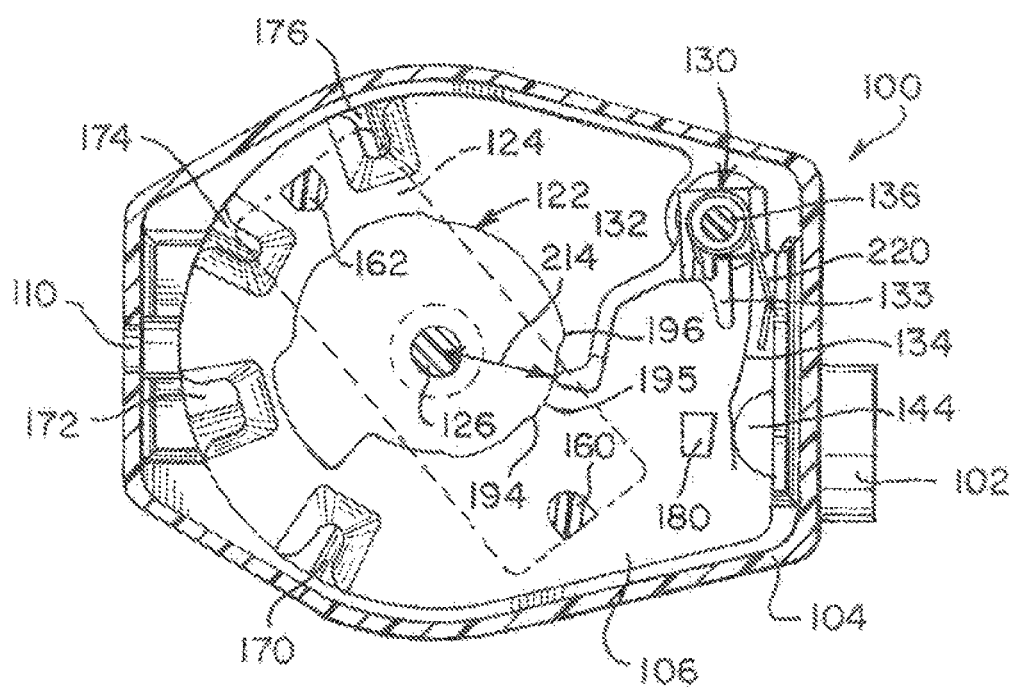
Figure 6D:
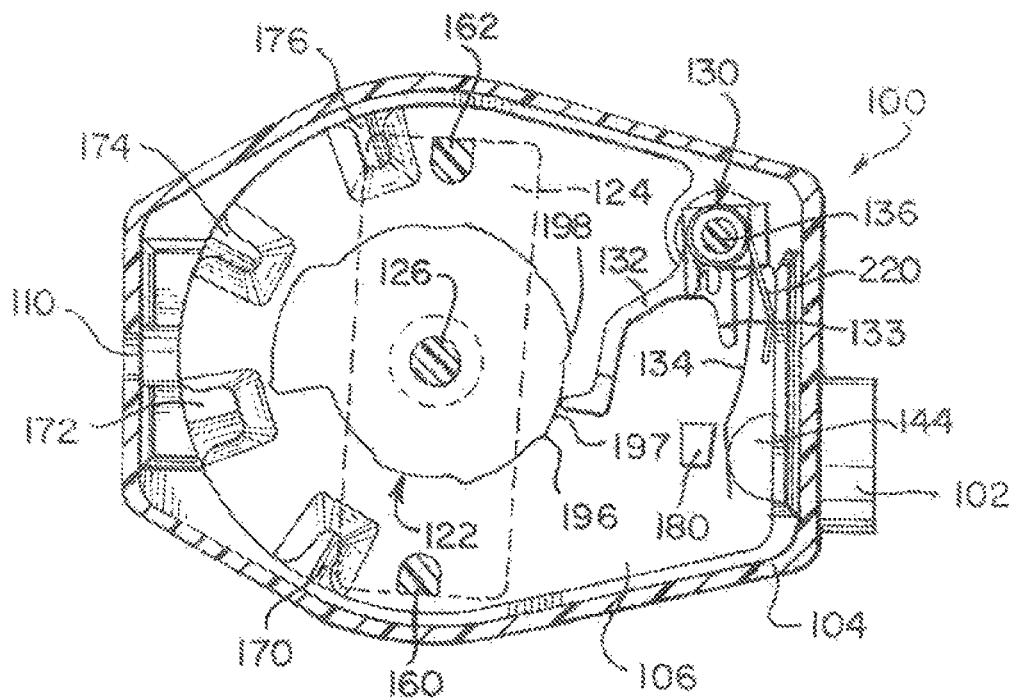

A third opening pressure setting is shown in FIG. 6C with rotor tooth 162 positioned between casing stops 174 and 176 such that cam follower 132 experiences only third cam surface 195 between points 194 and 196 at a third radial distance 214. To achieve a fourth pressure setting, FIG. 6D, both rotor teeth 160 and 162 are utilized relative to casing stops 170 and 176, respectively. Cam follower 132 is restricted thereby to fourth cam surface 197 between points 196 and 198.

Figure 6E:
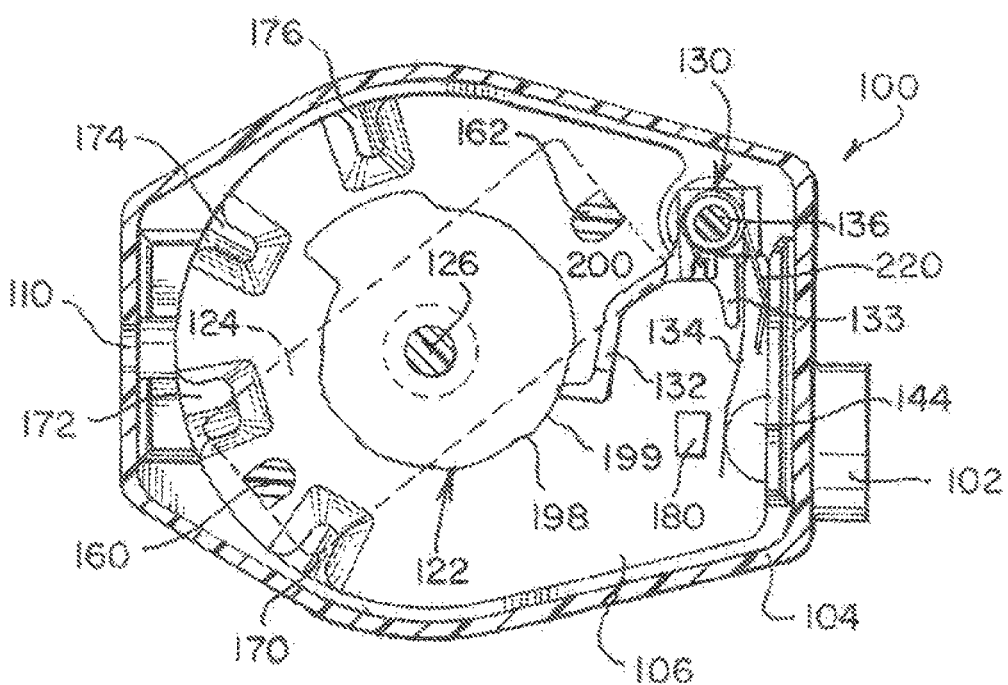
Figure 6F:
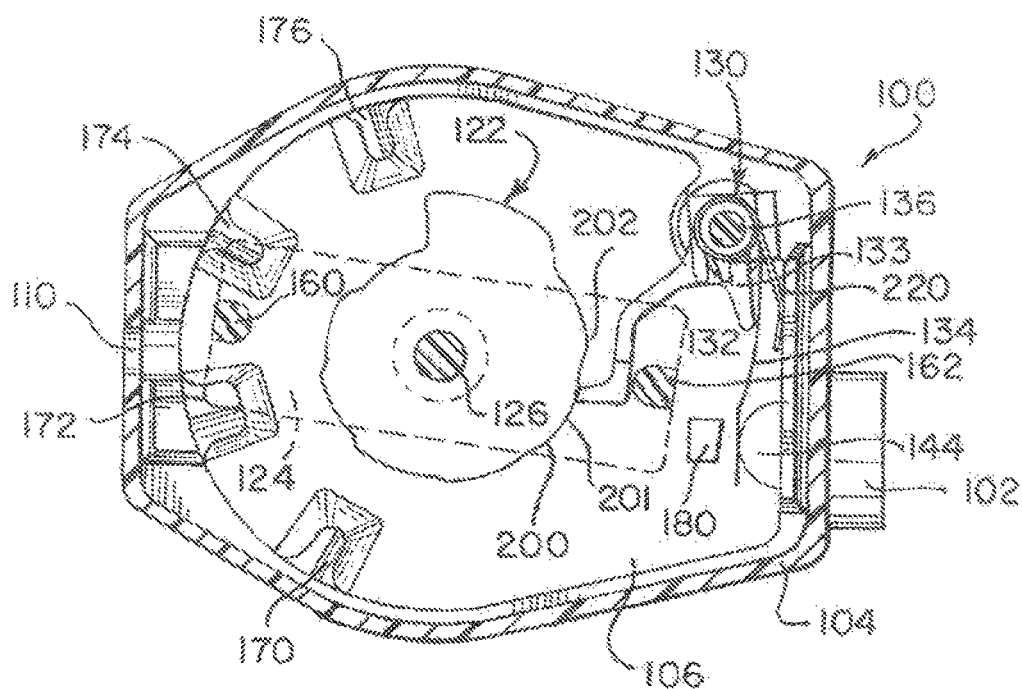
Figure 6G:
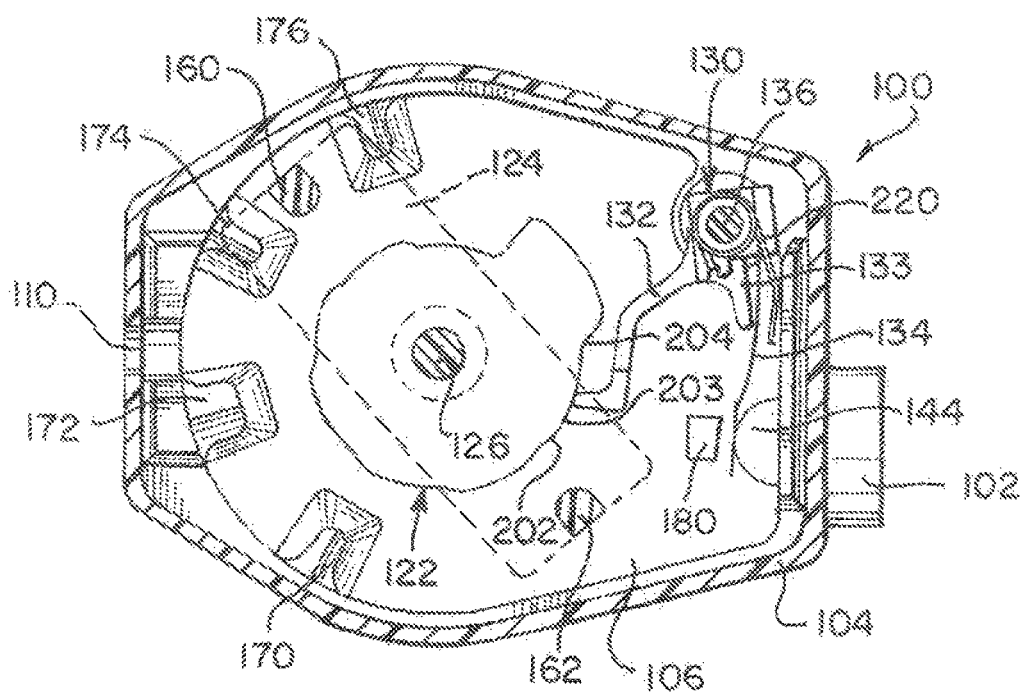

Fifth through seventh pressure settings are illustrated in FIGS. 6E-6G as rotor tooth 160 is successively captured between casing adjacent lock stop pairs 170-172, 172-174, and 174-176, respectively. Cam follower 132 is restricted thereby to fifth cam surface 199 between points 198 and 200, FIG. 6E, sixth cam surface 201 between points 200 and 202, FIG. 6F, and seventh cam surface 203 between points 202 and 204, FIG. 6G.

Preferred opening pressure settings currently range from approximately 30 mm to 210 mm water (294 Pa to 2,059 Pa) in seven increments of 30 mm (294 Pa), with a final, "virtual off" setting described in more detail below. Preferably, each valve unit is calibrated and tested at the time of manufacture at one or more flow rates. Actual opening pressure for each setting tends to vary according to flow rate, typically measured in milliliters per hour. Also, when tested with a 120 cm long distal catheter having an inner diameter of 1 mm, the average opening pressure typically will increase by 9 mm water or more at flow rates of 5 ml/h or more.

Figure 6H:
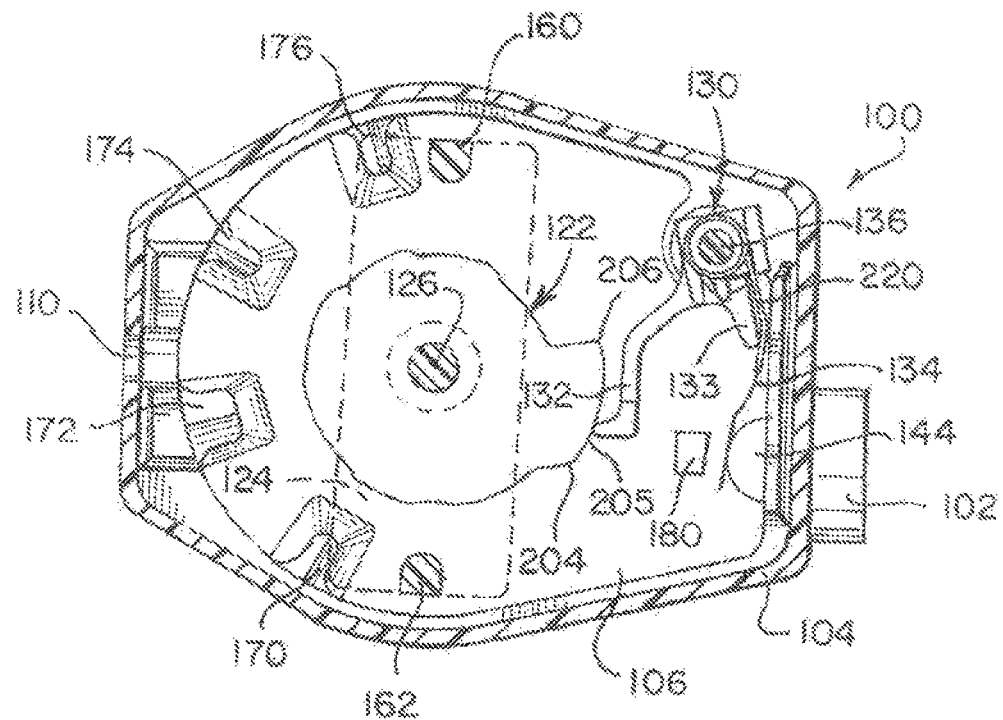

The final setting, FIG. 6H, of approximately at least 400 mm water (3,920 Pa) minimizes flow as a "virtual off" setting, that is, as substantially closed. This final setting is achieved by exposing cam follower 132 to outermost cam surface 205, defined by points 204 and 206, having greatest radial distance 218. This greatest cam setting forces stiffener element 133 of spring arm unit 130 against valve spring 134 to shorten its active, effective length and thereby dramatically increase the biasing force applied against ball 144. The final opening pressure is increased by more than fifty percent over the prior setting. In other constructions, a stiffener element is forced against a valve spring during two or more final cam settings at desired pressure increments.

Figure 9:
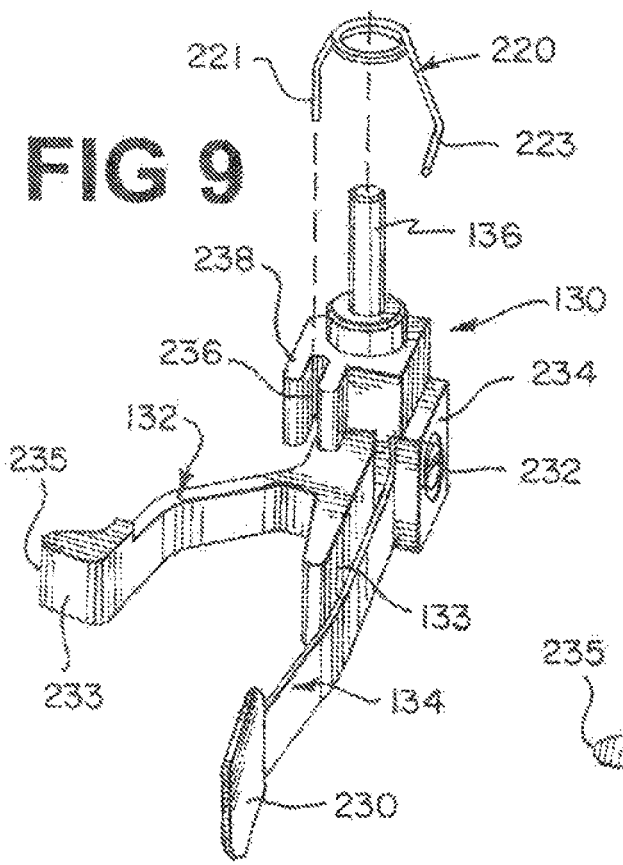
FIG. 9 is a perspective view of the spring arm unit with optional torsion spring.
Figure 9A:
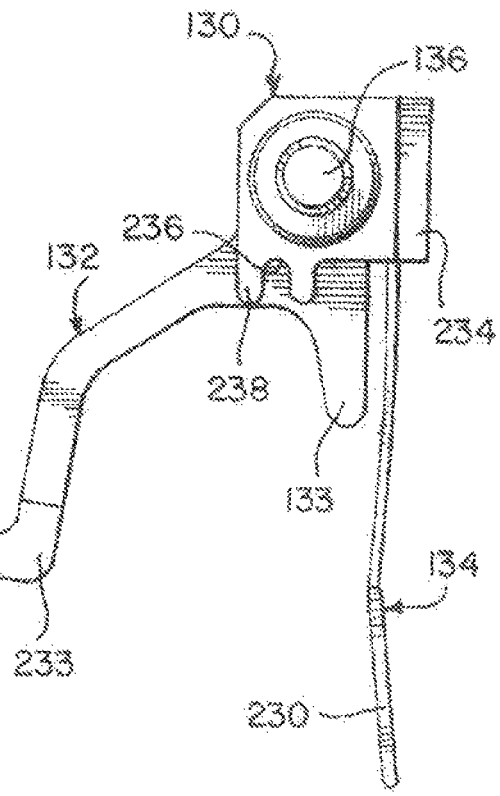
FIG. 9A is a top plan view of the element of FIG. 9.

Spring arm unit 130 is shown in greater detail in FIGS. 9 and 9A with cam follower 132, stiffener element 133, and valve spring 134. Cam follower 132 terminates in a triangular head 233 with rounded or chamfered edges, one of which serves as a bearing surface 235. In a preferred construction, spring element 134 is formed from stainless steel having a thickness of 0.020 inches and terminates in an enlarged pad 230 for contacting the valve ball or other movable valve member. In one construction, spring element 134 is attached to the remainder of spring arm unit 130 by a post 232 and rivet 234 which are secured by ultrasonic welding. Torsion spring 220 has a first leg 221 which is retained in recess 236 of projection 238. Second spring leg 223 rests against an inner surface of the casing.

Use of torsion spring 220 is optional, and is possible because only spring element 134 contacts the movable valve member. As a result, additional spring force from torsion spring 220 can be utilized to force bearing surface 235 of cam follower 132 against a cam surface of the rotor. This biasing force provided by torsion spring 220 augments rotational position of the spring arm reflective of the intended cam displacement without otherwise impacting the force applied to the ball or other movable valve member. This provides for a more accurate and repeatable opening pressure and a more manufacturable and robust design as it reduces the need to maintain minimal friction such as when the valve spring element solely provides the force needed to maintain the cam follower on the cam surface.

The position of the components and features within adjustable valve unit 100 at the first pressure setting shown in FIG. 6A is illustrated at a deeper partial cross-sectional view in FIG. 7. Opening 222 into the lower cam portion of rotor 120 inhibits negative pressure from developing under rotor 120, that is, opening 222 ensures pressure equalization as cerebrospinal fluid passes through valve unit 100.

The transition from the first pressure setting to the second pressure setting is illustrated in FIGS. 8 & 10 as rotor 120 is translated upwardly by magnetic attraction with an adjustment tool so that rotor tooth 162 is able to clear casing lock stop 172. Cam follower 132 is shown in FIG. 8 at point 192 passing from first cam surface 191 to second cam surface 193. Lower cam section 122 has a sufficient height relative to cam follower bearing surface 235 to ensure that cam follower 132 remains in contact with a cam surface of cam portion 122 in both the constrained and unconstrained conditions. Rotor retention spring 150, FIG. 10, has been compressed, its biasing force being overcome by magnetic attraction between rotor 120 and the adjustment tool while it is positioned over valve unit 100. Also illustrated in FIG. 10 are upper and lower synthetic ruby bearings 242 and 139 for upper and lower axles 136 and 138, respectively, of spring arm unit 130. Synthetic ruby bearing 240 rotatably supports rotor axle 126.

The position of the components and features within valve unit 100 at the final, "virtual off" or substantially closed setting shown in FIG. 6H is depicted at a shallower cross-sectional view in FIG. 11 in an unconstrained condition. Further clockwise rotation of rotor 120 is prevented by rotation stop or limiter 250 which projects downwardly from upper casing 104 to contact finger 127. Rotation stop 250 contacts the opposite surface of finger 127 when rotor 120 is turned fully counter-clockwise in an unconstrained condition. The actual position of rotation stop 250 may be shifted to the right of the position shown in FIG. 11 so that cam follower 132 is able to track nearly the entire portion of cam surface 205. Preferably, one side of stop 250 prevents rotor movement from the lowest setting directly to the highest setting and prevents the cam follower from touching the cam projection for the highest setting when the rotor is at its lowest setting. The other side of stop 250 prevents movement from the highest setting directly to the lowest setting. A side, partial cross-sectional view of rotation stop 250 blocking rotor housing 124, as well as spring 150 compressed between rotor 120 and upper casing 104, is shown in FIG. 12 for this unconstrained condition.

Figure 13:
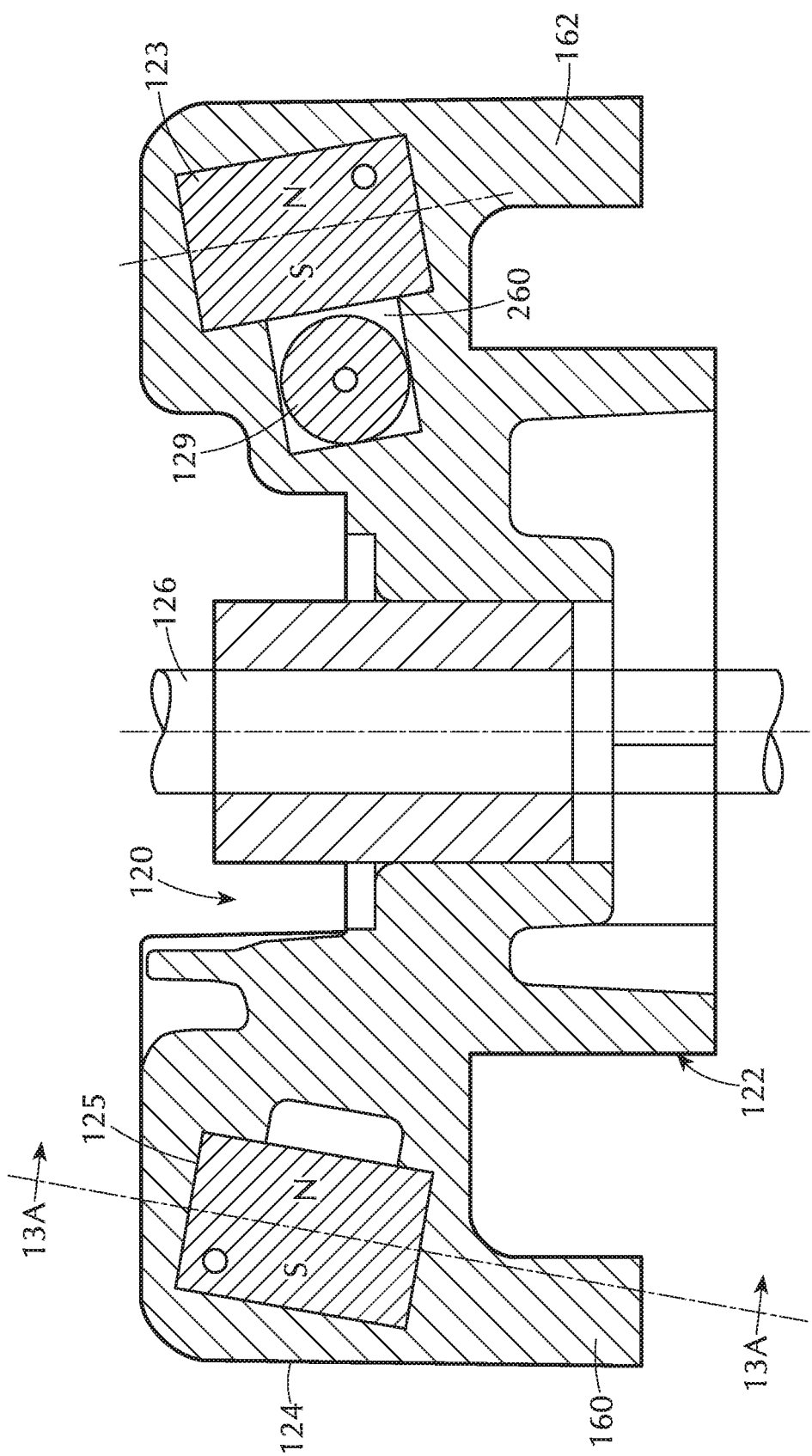
FIG. 13 is a side cross-sectional view along lines 13-13 of FIG. 11.

Further detailed views of selected features and components of rotor 120 in one construction are illustrated in FIGS. 13 & 13A. In particular, the housing portion 124 is shown as integral with cam portion 122. Pocket cavity 260, FIG. 13, contains magnet 123 and tantalum reference ball 129 which is readily visible during imaging of the valve unit 100 after implantation in a patient to confirm the actual pressure setting. Pocket cavity 262 holds magnet 125. A partial end view of housing portion 124 through magnet 125, pocket 262 and rotor tooth 160 is provided in FIG. 13A.

Figure 6I:
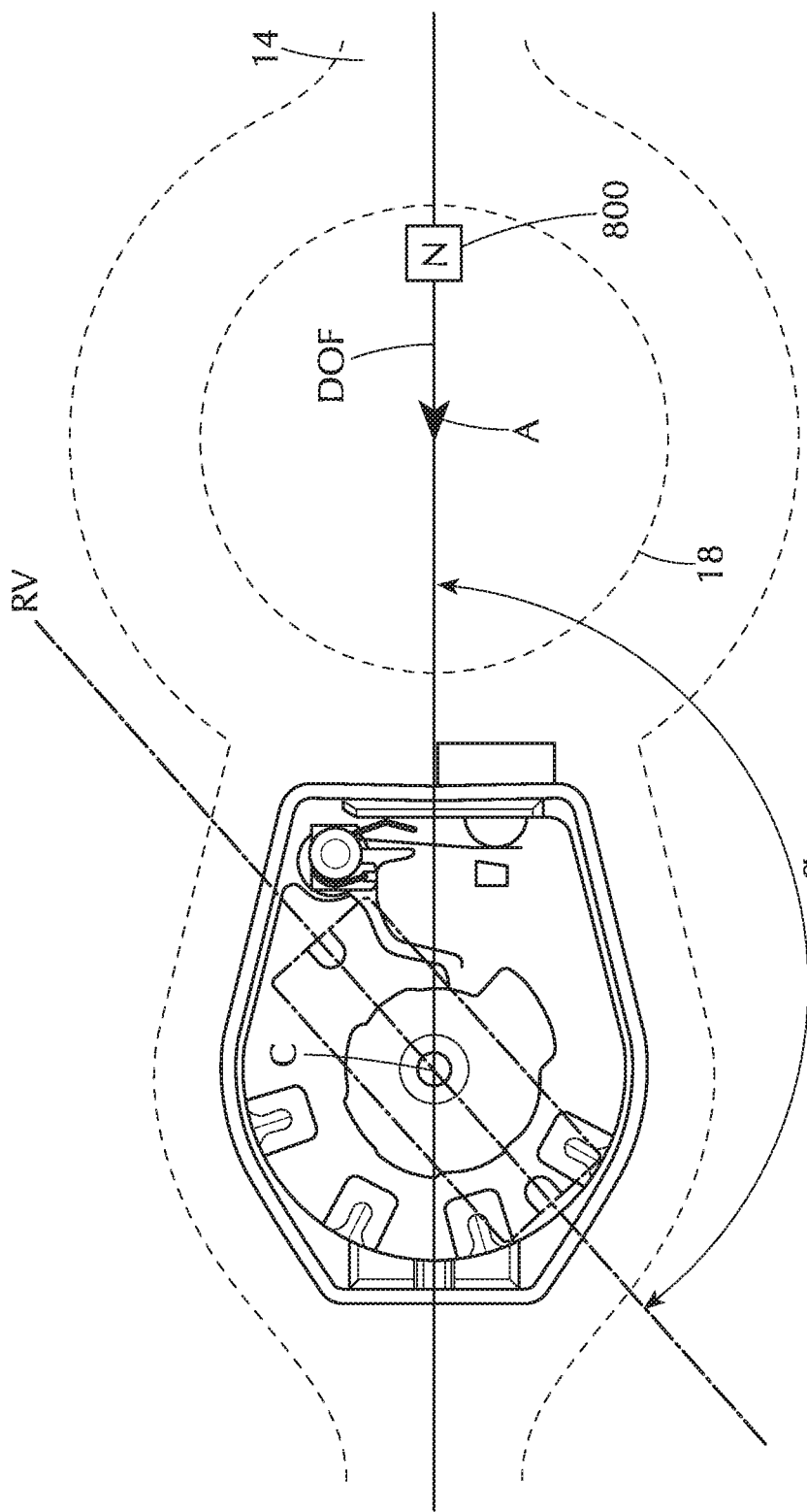
FIG. 6I is a partial cross-sectional view of the adjustable valve unit of FIG. 4 at an exemplary first pressure setting illustrating the arrow marking on the programmable valve device denoting a direction of fluid flow therethrough and the fixed reference magnet.
Figure 6J:
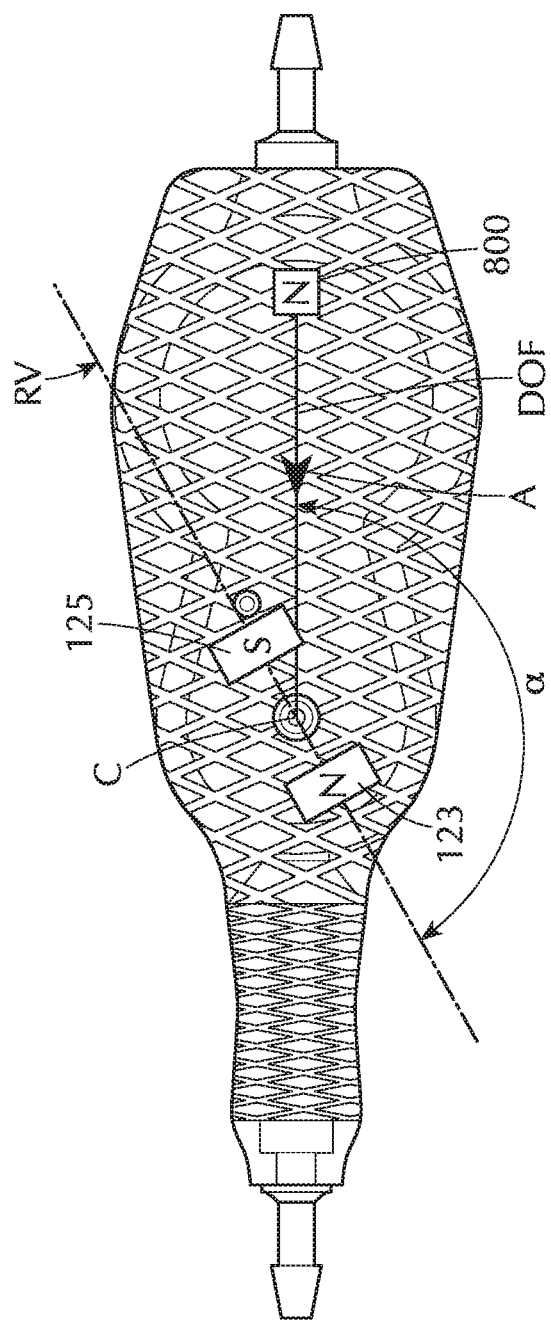
FIG. 6J is a top view of the programmable valve device of FIG. 1 wherein the adjustable valve unit is at the same first pressure setting illustrated in FIG. 6I and also showing the direction of flow arrow marking and positioning of the fixed reference magnet.

As previously mentioned, the programmable valve (FIG. 1) includes the fixed reference magnet 800 in addition to the primary magnetic elements 123, 125 disposed in the housing 124 of the rotor 120 of the adjustable valve unit, as illustrated in FIG. 6I. Referring to FIG. 6J, preferably, the fixed reference magnet 800 is located between the proximal connector 14 and the sampling/pumping chamber 18 within the direction of flow of the shunt valve. Preferably, fixed reference magnet 800 has a different magnetic strength from the primary magnetic elements 123, 125 and a different nominal distance between magnets (i.e., distance between reference magnet 800 and primary magnet 123 compared to distance between primary magnets 123 and 125) for proper identification. Nominal distance between primary magnetic elements 123, 125 is approximately 5.48 mm as measured from bottom inner corner to bottom inner corner. Fixed reference magnet 800 nominal distance is approximately 17.5 mm from RC axle to leading edge of reference magnet 800. Fixed reference magnet 800 is aligned with an arrow indicia or marking "A" on the programmable shunt valve 10 itself denoting the direction of flow of fluid therethrough and a rotation construct center point "C" midway between the magnetic elements 123, 125. A line passing through these three points (referred to as a direction of flow line) is the basis for determining the orientation of the programmable shunt valve 10, as discussed in detail further below.

Figure 14:
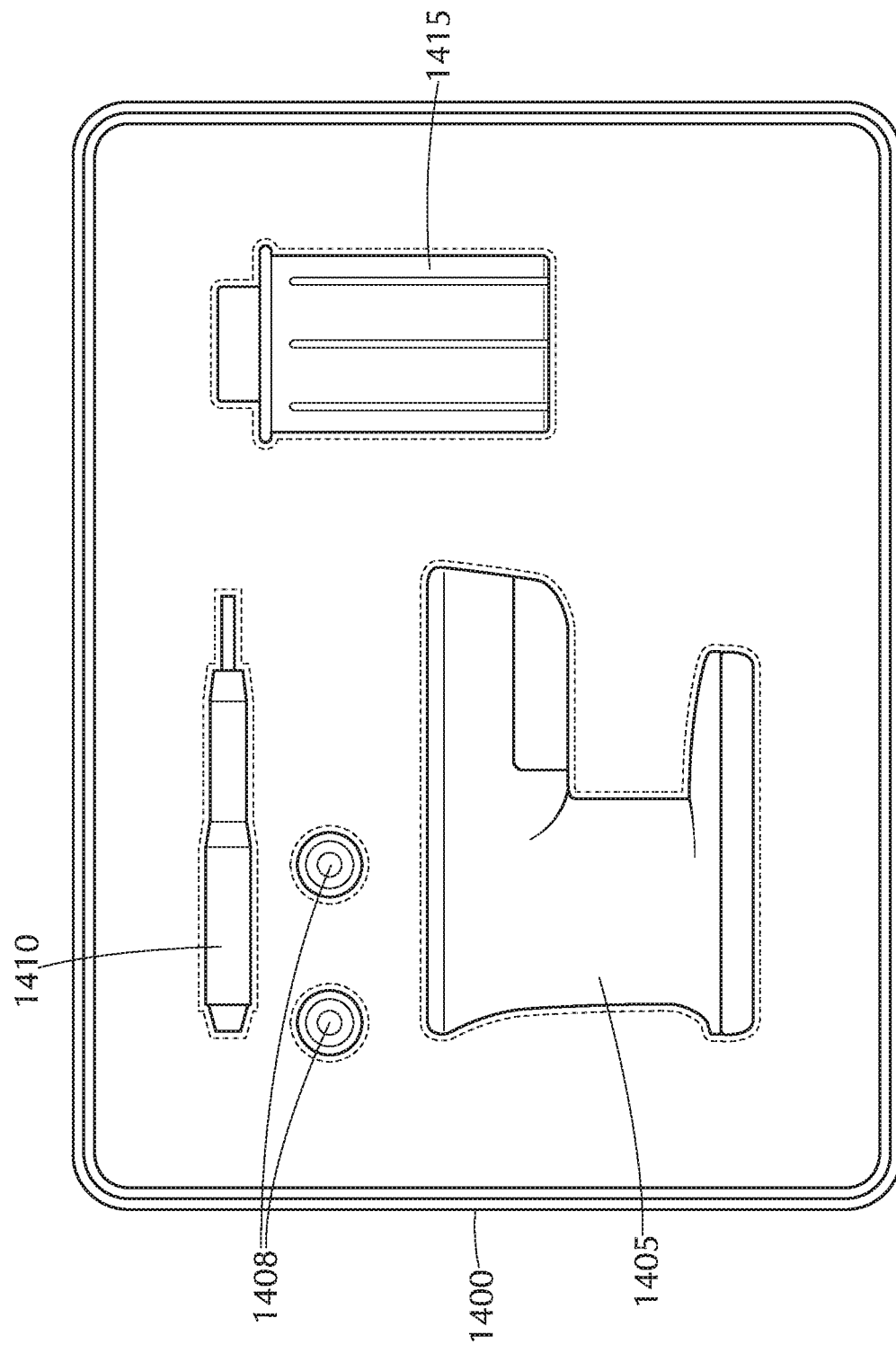
FIG. 14 is a perspective view of a tool set including an integrated locator/indicator tool, an adjustment tool and a screwdriver.

Pressure settings for valve units are noninvasively operated (i.e., valve located, current setting/indication readable and new setting adjustable) using several accessories, tools or devices referred to collectively as a toolset or toolkit. FIG. 14 shows an associated toolset 1400, preferably stored in a case, intended for use with the programmable valve of FIG. 1 having a fixed reference magnet 800. Toolset 1400 includes an integrated locator/indicator tool 1405, an adjustment tool 1415, a screwdriver 1410 and one or more spare batteries 1408. It is noted that the toolset may be modified in accordance with the present invention so that none, some or all of the tools in the toolset are integrated.

Figure 14A:
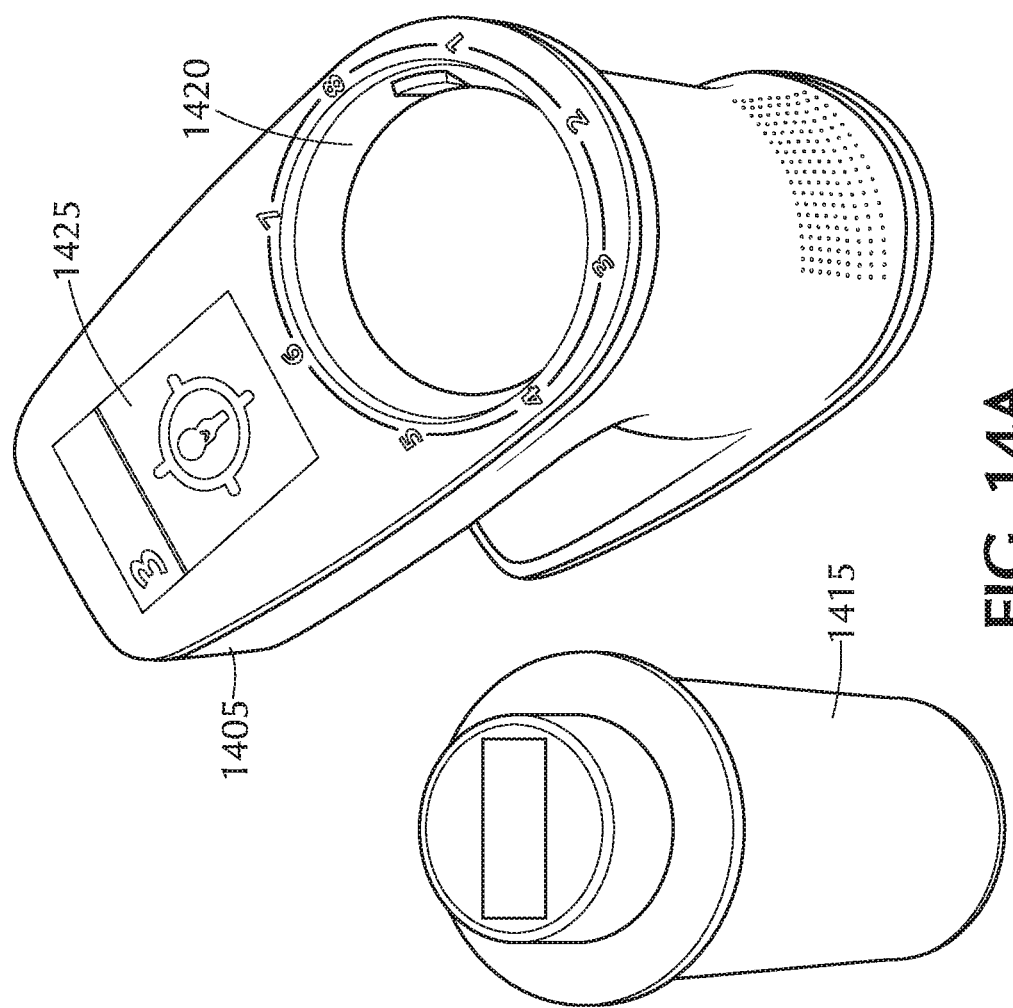
FIG. 14A is a top perspective view of the integrated locator/indicator tool and adjustment tool of FIG. 14, prior to the adjustment tool being inserted into the integrated locator/indicator tool.
Figure 14B:
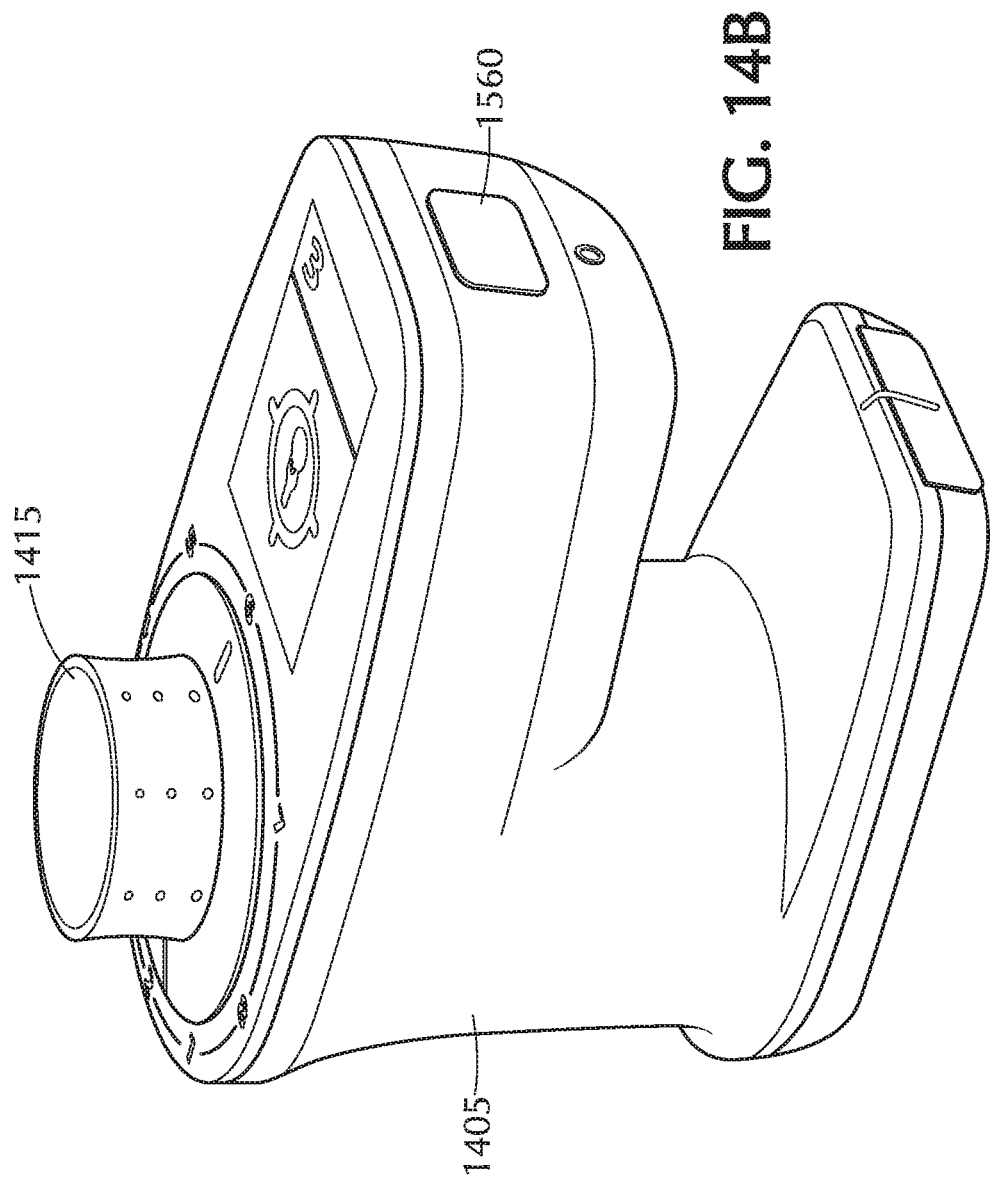
FIG. 14B is a top perspective view of the integrated locator/indicator tool and adjustment tool of FIG. 14, with the adjustment tool inserted into a complementary cavity in the integrated locator/indicator tool.

A top perspective view of the integrated locator/indicator tool 1405 and adjustment tool 1415 of FIG. 14, prior to the adjustment tool 1415 being inserted into a cavity 1420 of the integrated locator/indicator tool 1405, is shown in FIG. 14A. While FIG. 14B shows the adjustment tool 1415 following insertion into the cavity 1420.

Figure 15:
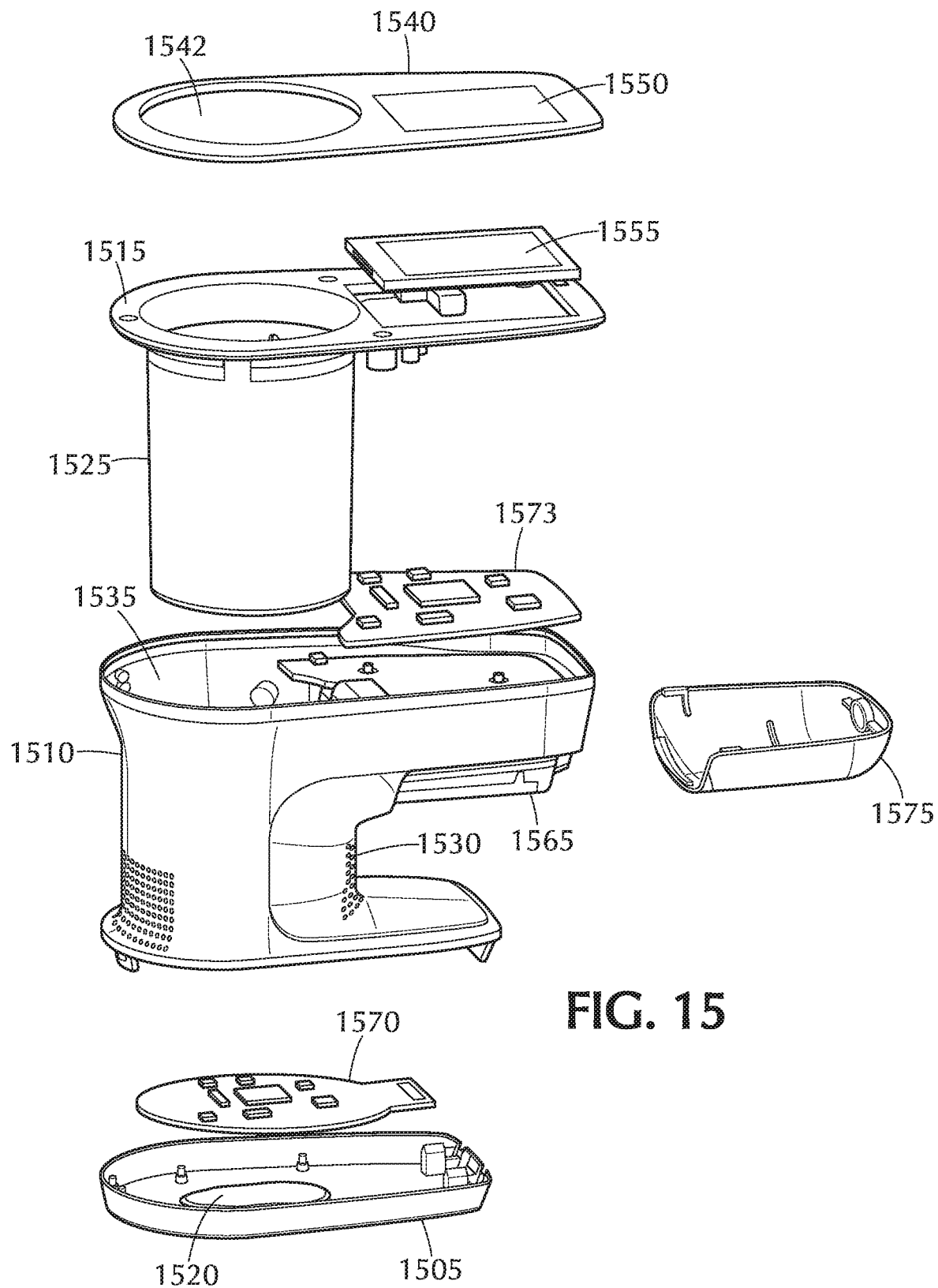
FIG. 15 is an exploded perspective view of the integrated locator/indicator tool of FIG. 14.

FIG. 15 is an exploded perspective view of the integrated locator/indicator tool 1405 of FIG. 14 which includes a housing. In the illustrated example, the housing comprises a bottom housing section 1505, a middle housing section 1510 and a top housing section 1515, each separate from one another. A cylindrical shaped section 1530 of the middle housing section 1510 defines a passageway or channel 1535 extending longitudinally therethrough. Top housing 1515 has a chimney 1525 complementary in size and shape to be received within the passageway or channel 1535 of the cylindrical shaped section 1530 of the middle housing section 1510. Chimney 1525 is closed at one end and open at an opposite end. The open end of the chimney 1525 receiving therein the adjustment tool 1415, as described in detail below. An exterior surface of the bottom housing 1505 has a recess 1520 defined therein that is complementary in shape and size to the outer contour of the programmable implantable bodily fluid drainage valve. In use, the integrated location/indication tool 1405 is positioned with the exterior surface of the bottom housing 1505 against the skin of the patient and the implantable bodily fluid drainage valve seated within the recess 1520. A top covering or layer 1540 may be mounted to the top of the assembled housing. Such covering or layer 1540 has a complementary size and shape opening 1542 to that of the chimney 1525. Disposed about the perimeter of the opening 1542 are a series of markings representing the different valve settings in predetermined increments (e.g., 1, 2, 3, 4, 5, 6, 7, 8). A second opening 1550 in the top covering or layer 1540 permits viewing therethrough of a display 1555, such as a Liquid Crystal Display (LCD). The integrated locator/indicator tool 1405 is powered by one or more batteries 1408 and turned ON/OFF by a button 1560. Batteries 1408 are housed within a battery enclosure assembly 1565 that includes a tray with electronic contact terminals between which the batteries are inserted. Access to the battery enclosure assembly 1565 for insertion/ removal of the batteries therefrom is via a removeable battery door assembly 1575. A two-dimensional array of 3-axis magneto-resistive sensors 1570 printed on a circuit board individually detects the magnetic field pattern produced by each primary magnetic element 123, 125 disposed in the housing 124 of the rotor 120 and the fixed reference magnet 800. It is within the intended scope of the present invention to substitute other types of sensor arrays capable of detecting magnetic fields, such as Hall sensors, for the 3-axis magneto-resistive sensors 1570. Another printed circuit board 1573 includes a processor/controller and memory device.

Figure 16:
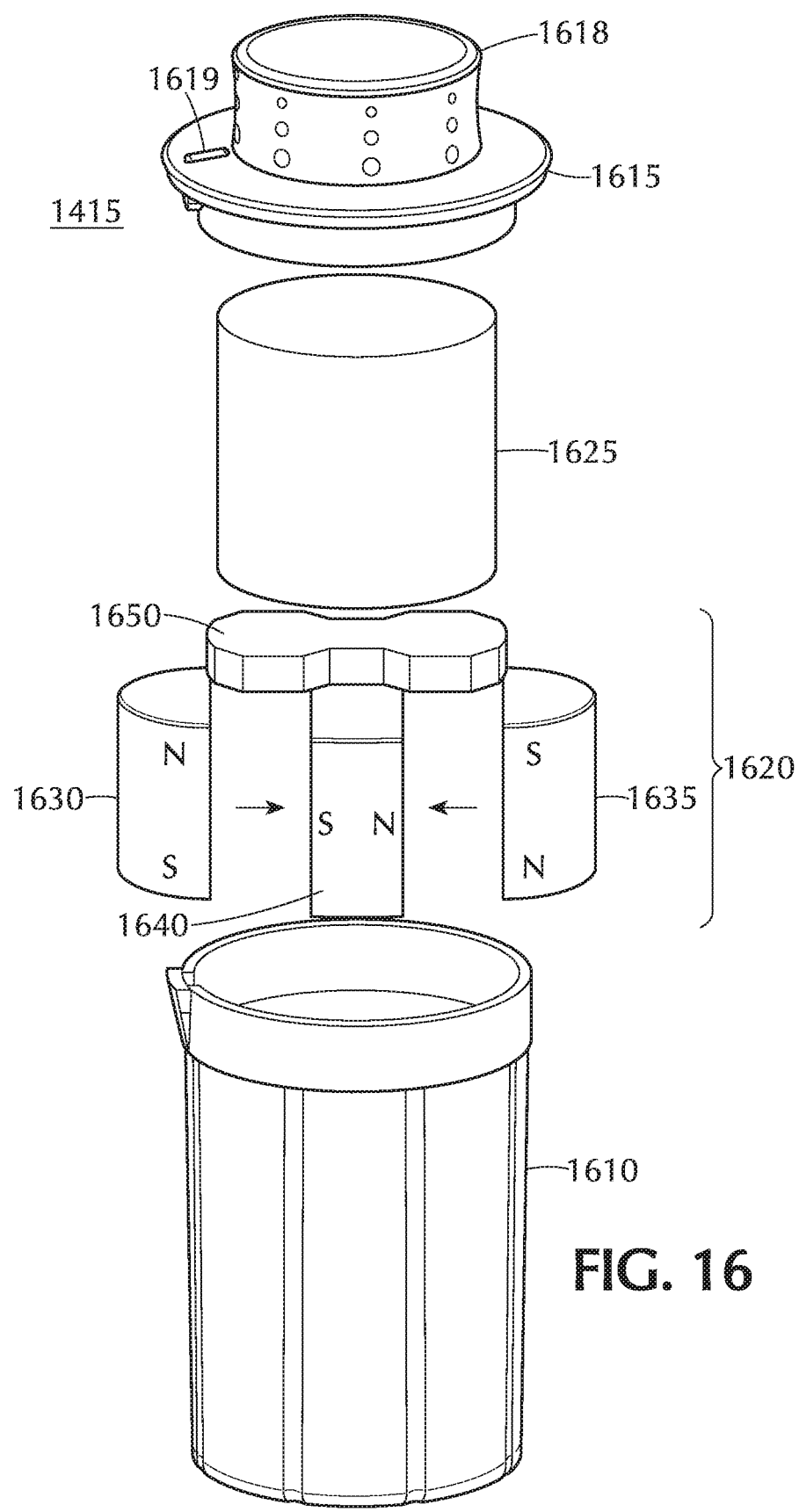
FIG. 16 is an exploded perspective view of the adjustment tool of FIG. 14.
Figure 16A:
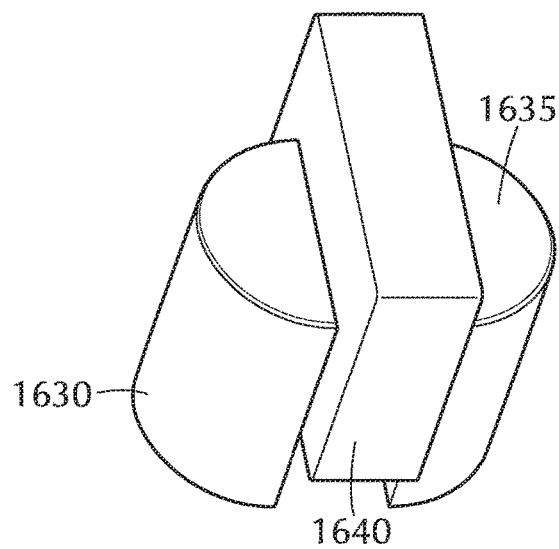
FIG. 16A is a perspective view of the placement of the half round magnets on either side of the magnet shield comprising part of the magnet assembly of FIG. 16.
Figure 16B:
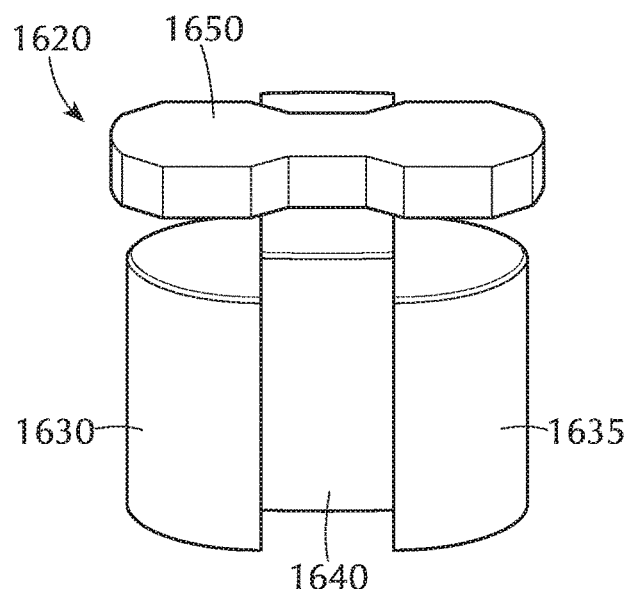
FIG. 16B is a perspective view of the assembled magnet assembly of FIG. 16.
Figure 16C:
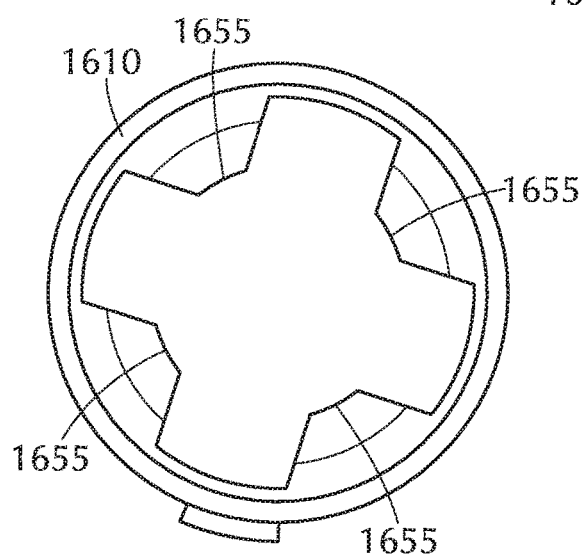
FIG. 16C is a top view of the assembled bottom and middle housing sections of the adjustment tool of FIG. 16 showing the internal vertical ribs.
Figure 16D:
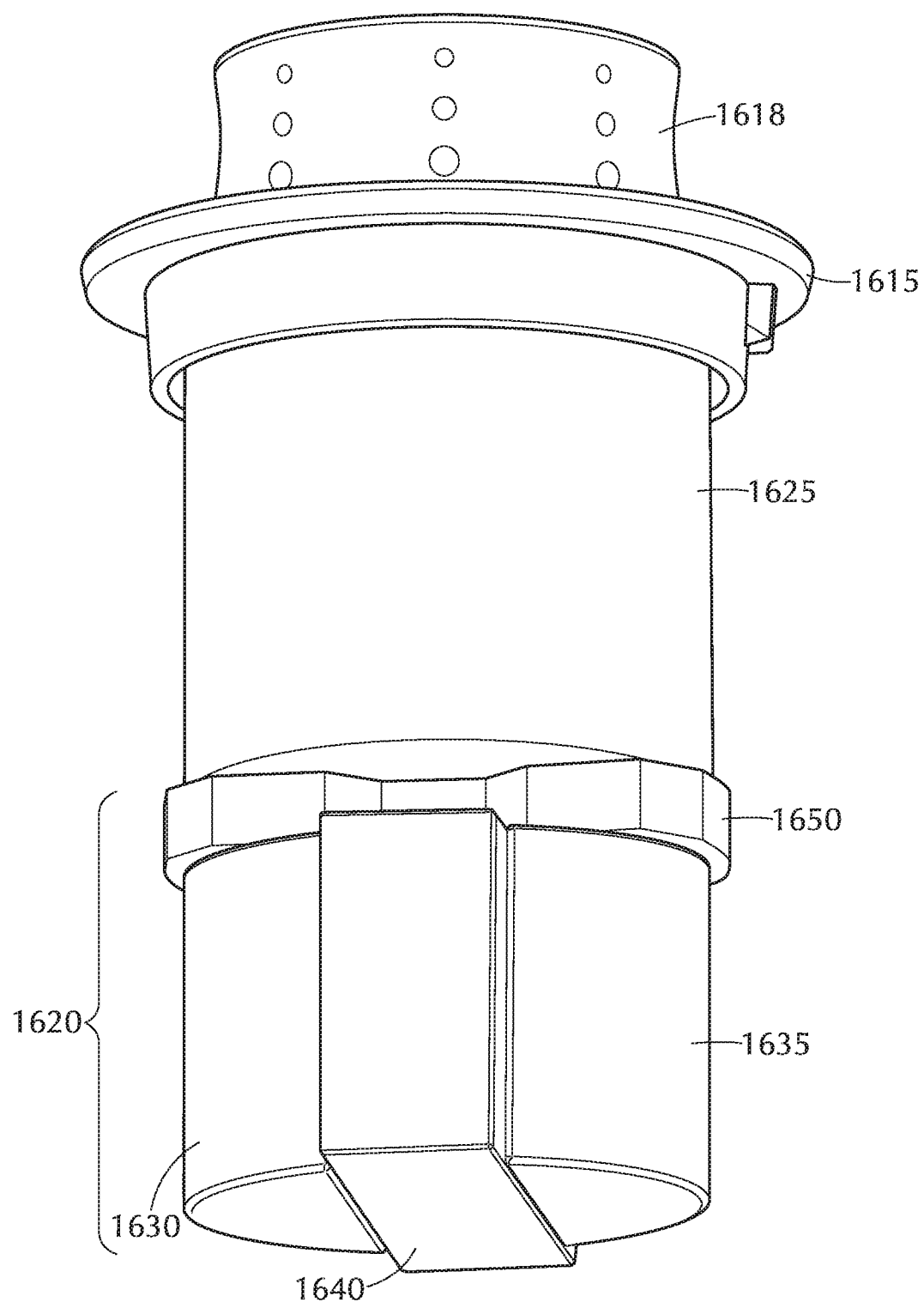
FIG. 16D is a perspective view of the assembled adjustment tool of FIG. 14 without the outer housing section to illustrate the magnet assembly.

FIG. 16 is an exploded perspective view of the adjustment tool 1415 of FIG. 14. The adjustment tool used to change the valve setting includes one or more magnetic elements (e.g. magnets or electromagnetic coils). In the illustrated example, a housing comprises an outer housing section 1605 and a top housing section 1615, each separate from one another. A magnet assembly 1620 is disposed in the outer housing section 1610. In particular, the magnet assembly 1620 in FIG. 16A is a Halbach array comprising two half round magnets 1630, 1635 connected by a yoke 1650 and separated by a shield magnet 1640 that redirects the magnetic field allowing deeper penetration. The strength of the half round magnets 1630, 1635 selected for use in the adjustment tool 1415 depends on one or more factors, such as distance from the valve and the design of the sensor array. The two half round magnets 1630, 1635 are rotated until their flat side lays flush against the magnet shield 1640. The orientation of the magnets 1640, 1630, 1635 should preferably be as shown in FIG. 16 with the magnet north side of the shield magnet 1640 in contact with the half round magnet 1630, 1635 with a magnetic north pointed toward the bottom of the outer housing section 1610. One of the two half round magnets 1630, 1635 faces the tantalum reference ball 129 (FIG. 13). The shield magnet 1640 is partially repelled by the half round magnets 130, 1635 and thus is held down by a yoke 1650 mounted on top of the shield magnet 1640 that, when assembled, is also in contact with the two half round magnets 1630, 1635. It is these components of the magnet assembly 1620 that when assembled together are inserted into the outer housing section 1610 so that the two half round magnets 1630, 1635 are received in respective recesses 1655 defined in an interior surface of the outer housing section 1610 with the half round magnet facing the tantalum ball 129 facing towards the '1 to 8 stop'. As is visible in the top view in FIG. 16C, the outer housing section 1610 includes a plurality of vertical ribs 1655 with which the half round magnets 1630, 1635 connect. A cylindrical shaped spacer 1625 is positioned above the yoke 1650 (FIG. 16D). The top housing section 1615 with a marking indicator is secured to the outer housing section 1610 forming the assembled adjustment tool 1415.

The magnetic field pattern produced by the primary magnetic elements 123, 125 disposed in the housing 124 of the rotor 120 and the fixed reference magnet 800 is individually detected by the two-dimensional array of 3-axis magneto-resistive sensors 1570 of the integrated locator/indicator tool 1405. It is within the intended scope of the present invention to substitute other types of sensor arrays capable of detecting magnetic fields, such as Hall sensors, for the 3-axis magneto-resistive sensors 1570. Once these three magnets are independently detected, the rotation construct center point "C" midway between the two detected primary magnetic elements 123, 125 is located. The detected fixed reference magnet 800 is connected with the arrow indicia or marking "A" denoting the direction of flow on the implantable valve and the rotation construct center point "C" midway between the two detected magnetic elements 123, 125 to define a direction flow line as a reference line for aligning or orienting the integrated locator/indicator tool 1405 with the direction of flow line of the implanted valve. Once the user has properly centered and oriented the toolset over the valve mechanism the toolset will provide an indication of valve setting based on the angle of north/south poles and facilitate adjustment of the valve setting.

Figure 17E:
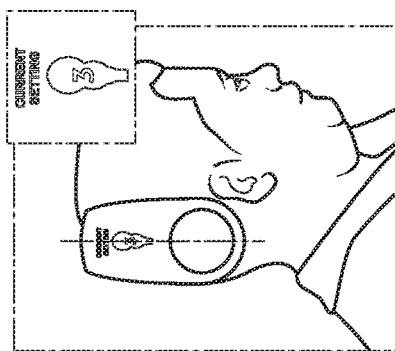
FIGS. 17A-17I are sequential illustrations of the steps for operating the electronic toolset in accordance with the present invention.
Figure 17D:
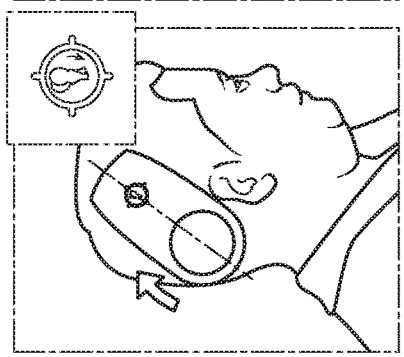
Figure 17C:
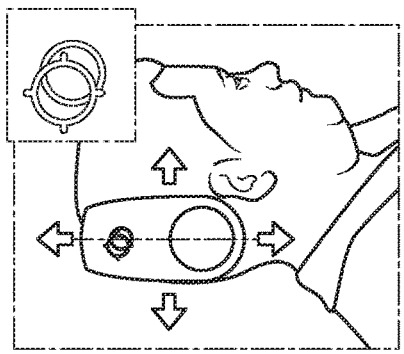
Figure 17B:
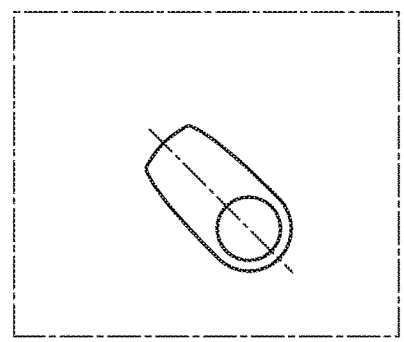
Figure 17A:
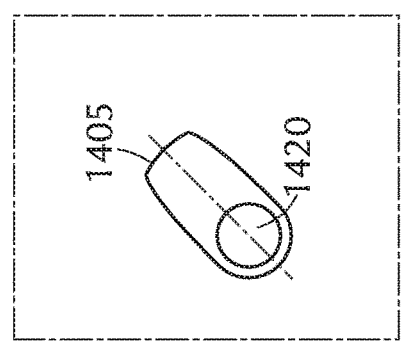
Figure 17I:
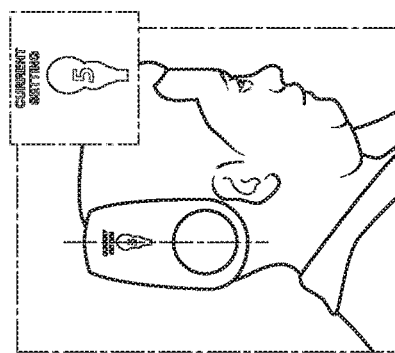
Figure 17H:
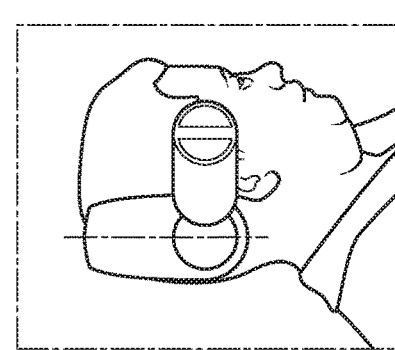
Figure 17G:
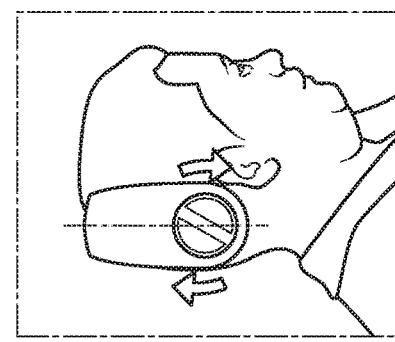
Figure 17F:
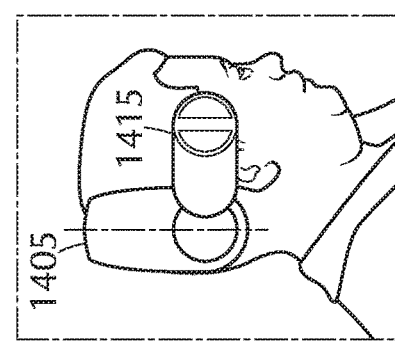

FIGS. 17A-17I are sequential steps in operation of the improved electronic toolset of FIG. 14 in accordance with the present invention. In FIG. 17A the integrated locator/indictor tool 1405 is powered on by pressing the power button 1560. Holding the power button 1560 for a predetermined period of time, e.g., approximately 3 seconds, calibrates, clears or zeros out the integrated locator/indicator tool 1405, as illustrated in FIG. 17B. Then a bottom surface (sensor floor) of the integrated locator/indicator tool 1405 is positioned against the skin above the implantable valve system such that the implantable valve is received in the complementary size and shaped recess 1520 defined in the exterior surface of the bottom housing section 1505, as illustrated in FIG. 17C. The integrated location/indication tool 1405 is moved in the appropriate direction (as indicated by the four arrows pointing in different directions) until the two circular visual images viewed on the LCD display 1555 are aligned with one another, indicating that the center of the adjustable valve unit 100 has been aligned with the center of the adjustable valve unit 100. Having centered the locator/indictor tool 1405 above the adjustable valve unit 100, then in FIG. 17D, the integrated locator/indicator tool 1405 is rotated until the two visual icons (complementary in shape (key hole shaped) to the implantable valve) displayed within the two circular visual images are aligned with one another to orient the integrated location/indication tool 1405 in the proper direction of flow of the implantable valve. It is now that the integrated location/indication tool 1405 has been centered and oriented in a direction of flow of the implantable valve, that the current indication or valve setting is read and visually displayed on the LCD (FIG. 17E). If the current valve setting is to be changed or programmed to a new valve setting, then in FIG. 17F the adjustment tool 1415 is inserted into the cavity 1420 of the integrated location/indication tool 1405 and rotated until the reference marking 1619 on the adjustment tool 1415 is aligned with the marking on the top lens 1540 corresponding to the read current device setting. In FIG. 17G the adjustment tool 1415 is rotated clockwise to the marking on the top lens corresponding to the new valve setting. Once set to the new valve setting, in FIG. 17H the adjustment tool 1415 is removed from the integrated locator/indicator tool 1405 (while the integrated location/indication tool 1405 remains stationary in place) and this new valve setting is now automatically detected by the integrated location/indication tool 1405 and visibly displayed on the LCD 1555 (FIG. 17I). It is noted that the positioning of the integrated location/indication tool 1405 remains unchanged in steps 17E-17I. The improved electronic toolset eliminates the requirement or need to have to once again locate the center of the valve and then confirm the new valve setting following adjustment by the adjustment tool 1415.

Clearly, the integrated indicator/locator tool 1405 is specifically designed for use with operating (e.g., indicate and adjust) the programmable valve in FIG. 1 having the fixed reference magnet 800. That is, the sensor array 1570 of the integrated indicator/locator tool 1405 differentiates individually each magnet (e.g., fixed reference magnet 800, each primary magnetic element 123, 125). However, knowing that the particular valve implanted includes a fixed reference magnet requiring use with the associated toolset including a sensor array would require the patient first be X-rayed. Moreover, even knowing that the implanted valve employs a fixed reference magnet specifically intended to be operated using the toolset in FIG. 14 including the sensor array 1570, some medical personnel may have a preference for, more experience in using, or familiarity with a toolset that does not include the sensor array (not able to individually differentiate among the magnets and thus unable to determine the orientation or direction of flow of the implant electronically). It is therefore desirable for the programmable valve having a fixed reference magnet to be operable interchangeably with an intended associated toolset able to discriminate the magnets individually (i.e., using a sensor array) as well as toolsets incapable of individually discriminating the magnets (i.e., other than a sensor array).

Figure 28:
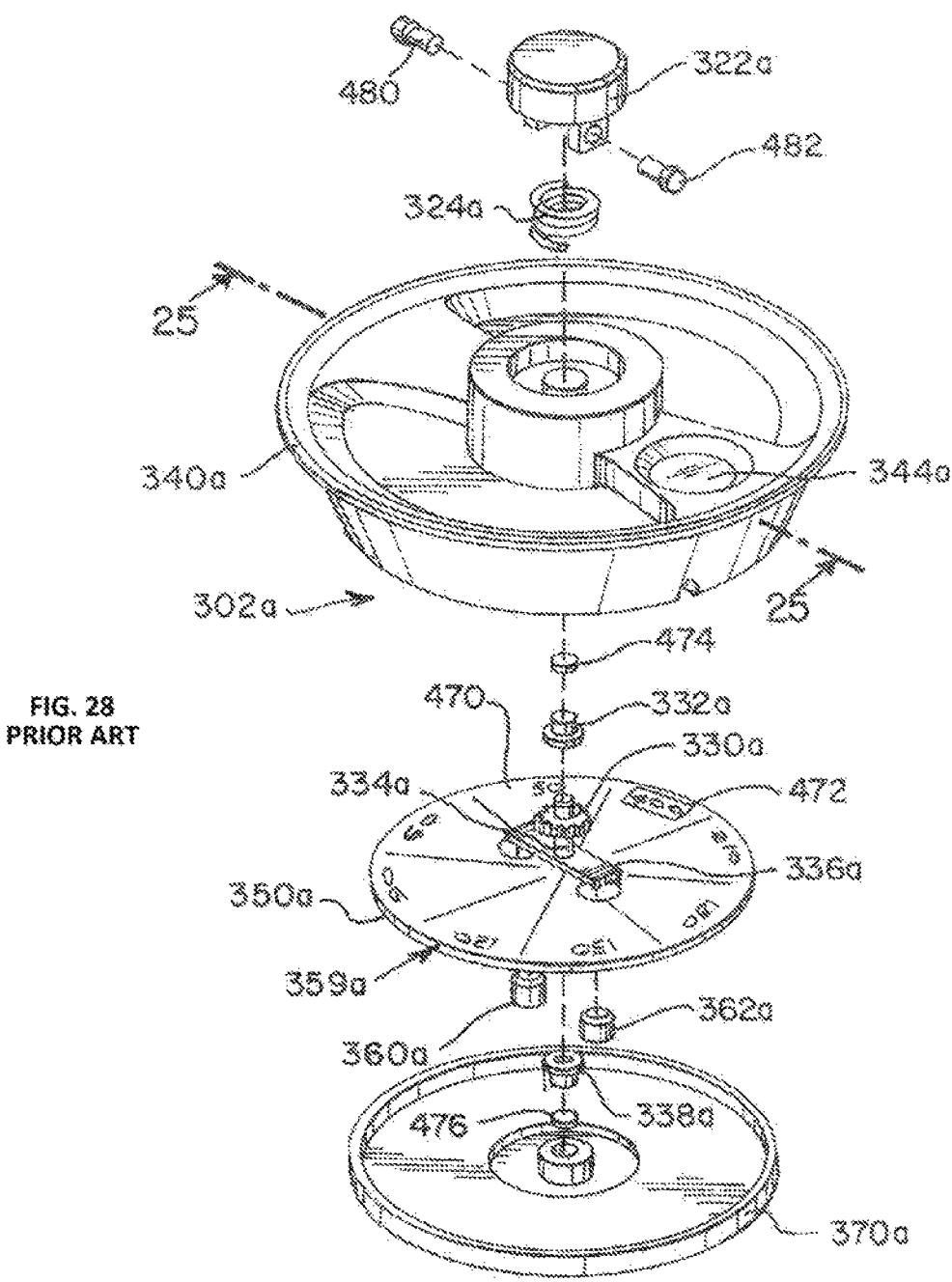
FIG. 28 is an exploded view of an alternative prior art indicator tool.
Figure 29:
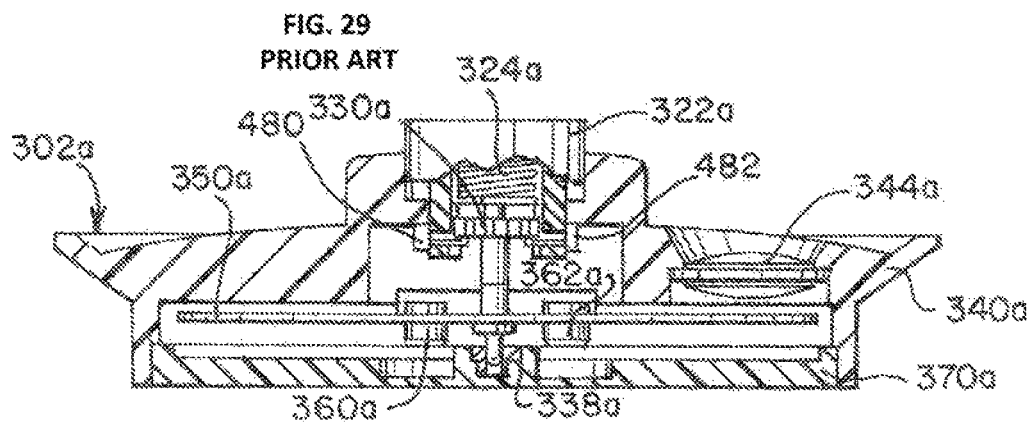
FIG. 29 is a side cross-sectional view along lines 25-25 of FIG. 28.

One prior art construction of such accessories incapable of individually discriminating among the magnets is illustrated in FIGS. 18-31 for toolset 300. This toolset includes a tool for detecting the configuration of the primary magnets associated with the rotation construct in what hereinafter is referred to as an analog manner or using an analog compass, described in further detail below. Such conventional toolset in FIGS. 18-31 is not capable of individually discriminating among the magnets (e.g., fixed reference magnet 800 and each primary magnetic element 123, 125). An alternative construction of a prior art indicator tool is shown in FIGS. 28 & 29 below.

Toolset 300 includes indicator tool 302, FIGS. 18, 19 and 22-24, a locator tool 304, FIGS. 18, 20, 21-24 and 26-27, and adjuster tool 306, FIGS. 18 and 25-27. Indicator tool 302 and adjuster tool 306 each can nest on top of locator tool 304, as shown and described in more detail below. As illustrated in FIG. 18, toolset 300 includes in this construction a storage and transport case 308 having a smaller recess 310 for carrying adjuster 306 and a larger recess 312 for carrying indicator 302 nested with locator 304. Preferably, indicator release button 322 of indicator 302 is received within upper recess 314 when case 308 is closed for storage or transport of toolset 300.

An exploded view of components for indicator tool 302 is provided in FIG. 19. A pressure wheel assembly 359 includes a value wheel 350 supported by yoke 336, which is fixed in track 337 of wheel 350, also referred to as a readout dial. A spindle 334 rotates easily and securely on synthetic ruby bearings 332 and 338 carried by indicator housing 340 and base 370, respectively, when wheel assembly 359 is in a released or unlocked condition. Wheel 350 carries a plurality of paddles or regions, such as paddles 352 and 354 having pressure value indicia 356 and 358, respectively. Another construction having a circular disc with indicia regions is shown and described below relative to FIG. 28. Magnets 360 and 362, FIG. 19, are carried in recesses 351 and 353 of wheel 350 and preferably are fixed with a retaining compound to metal yoke 336. In one construction, yoke 336 is formed of an alloy such as Ti6Al-4V. Magnets 360 and 362 have a known north-south polarity which is oriented relative to the various value indicia on the value wheel 350 so that the proper readout will be provided when the indicator tool is placed over an implanted valve unit.

When release button 322 is depressed from a first position to a second position, FIG. 23A, wheel assembly 359 enters a released condition and pressure value wheel 350 is able to rotate freely on spindle 334, FIG. 19. Spring 324 biases release button 322 upwardly so that gear 330 is normally engaged in the first position by at least one catch, such as inwardly facing projections 327 and 329, formed on downward button extensions 326 and 328, respectively, at the lower portions of button 322. Gear 330 is preferably a bevel gear, more preferably a crown gear as illustrated in FIG. 19, with at least one recess between teeth or cogs, preferably a pair of opposing recesses, for each pressure indicia to be read on wheel 350. When indicator tool 302 is positioned with locator tool 304 over a valve unit, such as shown in FIGS. 18-20, wheel assembly 359, FIG. 19, rotates freely like a compass after button 322 is depressed, until a north-south polarity is encountered that is stronger than the earth's magnetic field. Unlike a compass, wheel assembly 359 preferably can spin and properly indicate the actual setting of a valve unit regardless of the position or orientation of the indicator tool, even when indicator tool 302 is held vertically or upside-down.

Magnets 360 and 362 of indicator tool 302 are attracted to magnets in the valve unit to be read, such as magnets 123 and 125 of valve unit 100 as shown in FIG. 13, for example. When button 322 is released, spring 324 biases it back to the first position, and projections 327 and 329, FIG. 19, travel upwardly to engage with a pair of recesses which are closest to them to drive wheel assembly 359 to the closest setting and thereby lock pressure value wheel 350 so that one pressure value is clearly visible through lens 344 carried by window or opening 342 defined in upper housing 340. Button 322 can translate or reciprocate along indicator axis of rotation IR, but is incapable of rotation relative to indicator housing 340. Biased by spring 324, button 322 thereby drives wheel assembly 359 to a discrete pressure value position.

Indicator tool 302 may be easily lifted by a clinician from storage case 308 by grasping raised finger grip section 348. Indicator 302 is aligned with locator 304 so that marker 346, FIGS. 19 and 22, aligns with marker 380, FIG. 20, defined on flared surface 400 of locator tool 304. In some constructions, actual rotation of indicator 302 relative to locator 304 is prevented by a key, detent or other lock feature on one tool and a corresponding recess or matching interlock on the other tool. As shown in FIGS. 20 and 22A, for example, the interior of wall 383 of locator 304 carries a projection 384, preferably a metal stop, which mates with a recess 349 in the exterior of wall 347 of indicator 302 to align the two tools in a fixed relationship.

Locator tool 304 provides a fixed reference relative to an implanted shunt valve SV carrying a valve unit VU as shown in phantom in FIGS. 21, 23 and 24. Floor 381 of locator tool 304 defines a specially shaped upper opening 382, FIG. 20, which conforms to the implanted shunt valve SV, FIGS. 21 and 23. Additionally, lower skirt 386 of locator 304 defines openings 387 and 388 which receive distal catheter DC and ventricular catheter VC, respectively. Implanted components are shown in phantom in FIGS. 21 and 23, as are skin SK and skull SL of a patient.

Additional features on locator tool 304 are utilized with adjuster tool 306. The interior of wall 383 defines a series of reference points such as recesses 392 and 394, FIG. 20, each of which can receive a detent such as ball 426 biased by spring 424 within receptacle 422, FIGS. 25 and 26A, carried by rim 428 of adjuster 306. It is desirable to have a least one of a tactile and audible indication, such as a click sound and feel, when ball 426 engages one of the recesses 392 or 394. Also, flared surface 400 carries pressure value indicia such as lowest pressure setting 402 and highest pressure setting 404, FIG. 20, which serve as starting points for adjuster tool 306, as described below.

Typically, a shunt valve having a valve unit according to the present invention is initially adjusted before implantation while it is still in a sterile package. Preferably, the package has a reference indicia such as an arrow. Locator tool 304 is placed over the shunt valve so that marking 380, FIG. 20, or a marking (not shown) on the underside of floor 381, aligns with the package arrow. Indicator tool 302 is then fully seated into locator tool 304 so that indicator marking 346, FIGS. 19 and 22, is aligned with locator marking 380. Button 322 is depressed and held, such as shown in FIG. 23A, until wheel 350, also referred to as a readout dial, stops moving. Button 322 is then released. The current valve setting will be visible in indicator tool window or opening 342, through lens 344, FIG. 19. Indicator tool 302 is removed, with the current valve setting locked in position by the engagement of button projections 327 and 329 with gear 330 as described above.

While the shunt valve is still in its sterile package, adjustment tool 306 is inserted into locator tool 304 so that adjustment arrow 438 points to the valve setting number on the locator tool 304 which corresponds to the actual, current valve setting. The clinician holds the locator tool 304 with one hand and rotates adjustment tool 306 with the other hand until it points to the desired valve setting. Once the desired setting is achieved, the adjustment tool 306 is lifted straight upwards a minimum of approximately 3 cm (approximately 1.25 inches) before any horizontal motion is imparted to it to avoid possible resetting of the valve unit. It is also desirable to have the adjustment tool 306 spaced at least approximately 18 cm (approximately 7 inches) from the indicator tool 302 while reading the actual valve setting to avoid possible influence on the reading.

Adjustment tool 306 preferably provides an audible click and a tactile response as it is turned to each setting. Locator tool 304 defines a rotation stop, such as projection 384, FIG. 20, which prevents rotation of adjustment 306 directly from lowest setting 402 to highest setting 404, FIG. 20, or vice versa, to mimic the rotational limits on the valve rotor imposed by rotational stop 250, FIG. 11, for example. Adjuster tool 306 defines a channel 430, FIG. 25, bounded by a radially projecting arcuate stop 433 extending from edge 432 to edge 434, which allows the adjuster tool 306 to be rotated in either direction until an edge 432 or 434 of arcuate stop 433 contacts projection 380 of locator tool 304.

A similar procedure is utilized to percutaneously indicate and adjust the valve unit after implantation. The shunt valve is located by palpation. In one construction, the underside of floor 381, FIG. 20, of locator 304 carries an arrow, and that arrow is aligned with the direction of fluid flow through the implanted valve. Opening 382 of the locator tool 304 is centered around the valve unit as shown in FIG. 21. Indicator tool 302 is then placed fully into the locator tool 304 as shown in FIGS. 23 and 24 so that the markings 346 and 380 are aligned. The button 322 is depressed and held down, FIG. 23A, until the readout disc 350 stops moving. Button 322 is released and the current valve setting value is captured until button 322 is again depressed for the next reading. Indicator tool 302 then is removed.

Next, adjuster tool 306 is inserted into locator tool 304 as shown in FIGS. 26 and 27 so that arrow 438 is aligned with the current valve setting, which is not necessarily aligned with locator marking 380 as shown in FIG. 26. With one hand holding the locator tool 304, the clinician turns the adjuster tool 306 with the other hand until arrow 438 points to the desired valve setting. Preferably adjuster tool 306 provides an audible click and a tactile response as described above as it is turned to each setting.

After the desired setting is reached, adjuster tool 306 is lifted directly away from locator tool 304 without further rotation. Preferably, indicator tool 302 is then replaced into locator tool 304 and another reading is taken to confirm correct valve pressure setting. Alternatively, or in addition to re-use of the indicator tool, the implanted valve can be imaged with x-ray to confirm current valve setting.

Figure 25:
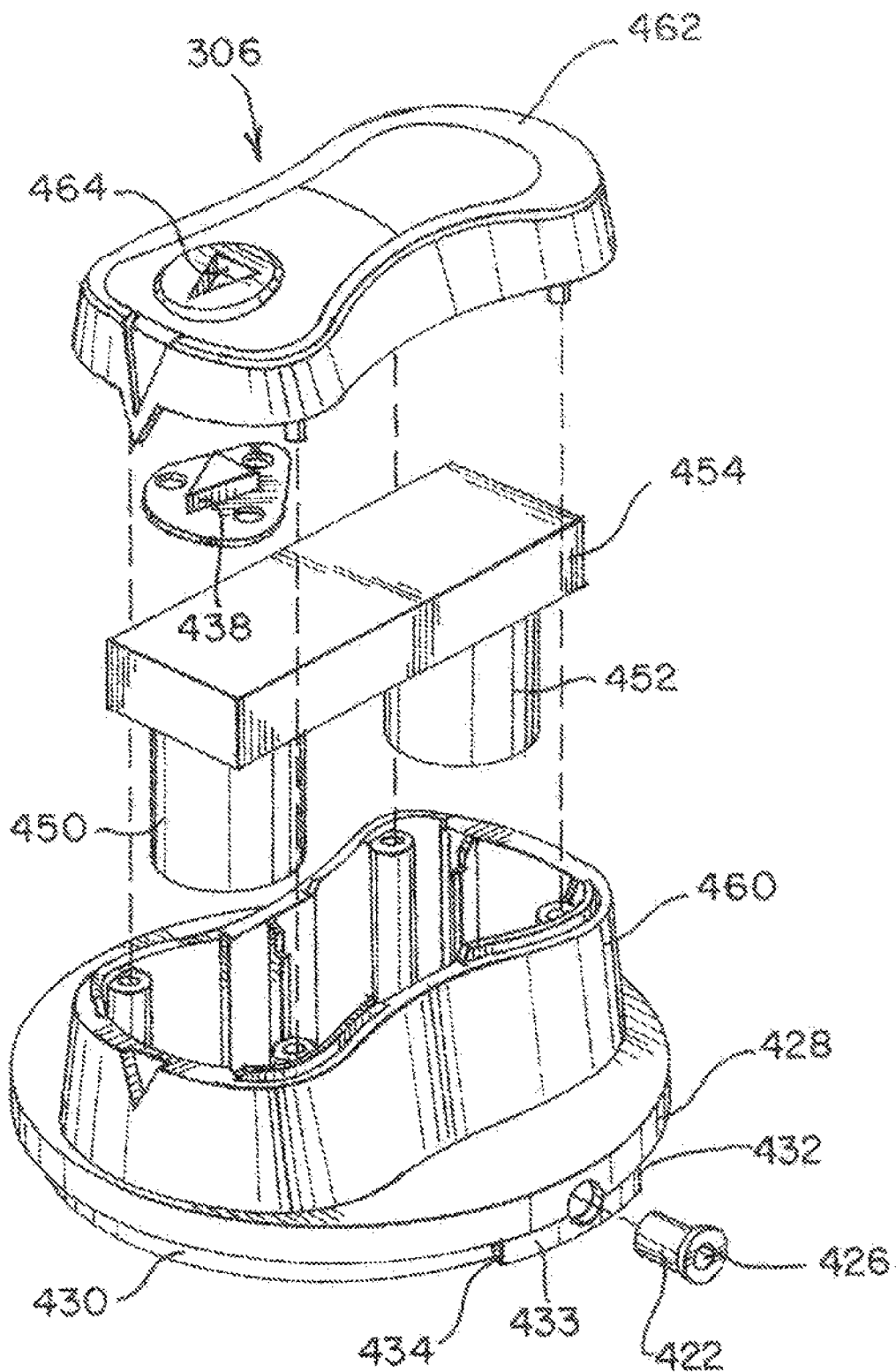
FIG. 25 is an exploded view of the setting adjuster tool of FIG. 18.

Returning to FIG. 25, components of adjuster tool 306 include a metal yoke 454, such as a bar of 416SS stainless steel, for supporting magnets 450 and 452 in a housing 460. Preferably, the poles of the magnets are aligned so that one magnet has a "north" polarity at its base while the other has an opposite, "south" polarity at its base. A cover 462 defines an opening 464 which receives arrow marker 438 in this construction as shown in FIGS. 25-27; in other constructions, marker 438 is integral with cover 462 or is applied to its surface after molding.

An alternative indicator tool 302a is illustrated in FIGS. 28-29 having a wheel assembly 359a including a circular readout dial 350a with numerical pressure value indicia such as a first, low setting 470 of "30" or "1", representing 30 mm water (294 Pa), and an eighth, high setting 472 of "400" or "8", representing 400 mm water (3,920 Pa) as a "virtual off" setting. Gear 330a is carried by metal yoke 336a, to which are attached magnets 360a and 362a, and spindle 334a, which turns freely on ruby bearings 332a and 338a supported by shims 474 and 476, respectively, when button 322a is depressed against the biasing force of spring 324a to move from a first, locked position to a second, released position.

Stops 480 and 482 of button 322a are catches that are shown engaging horizontal teeth of gear 330a in FIGS. 28 & 29 in the normal condition for indicator tool 302a. Also shown are housing bottom 370a and lens 344a carried in upper housing 340a.

Figure 30:
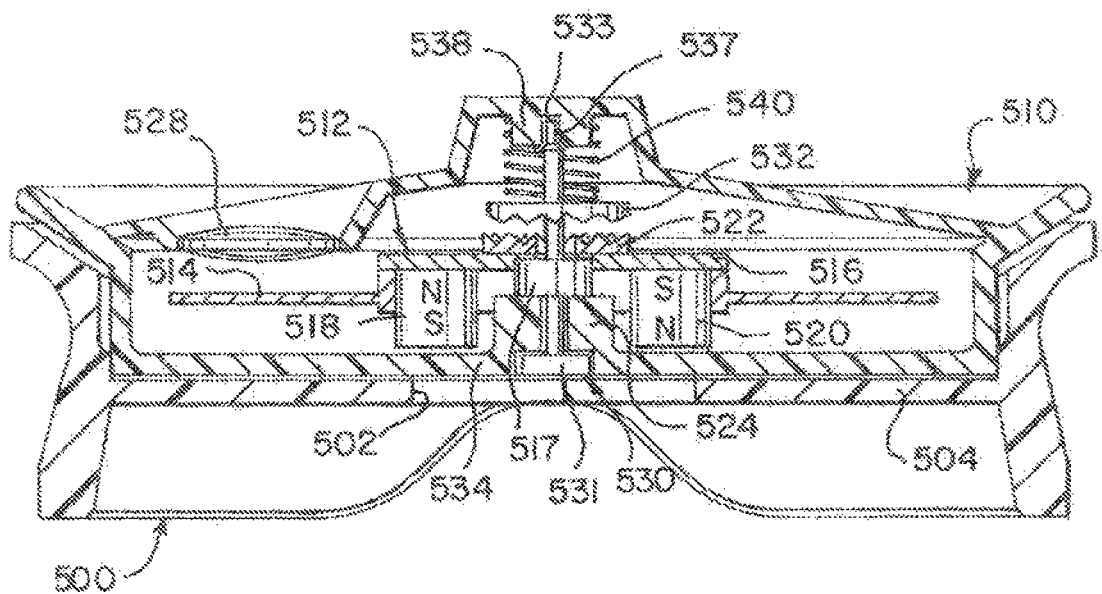
FIG. 30 is a cross-sectional view of another alternative prior art indicator tool positioned in a locator tool.

Yet another alternative construction of a prior art indicator tool is shown in FIG. 30 nested in a locator tool 500 defining an opening 502 in a floor 504. Indicator tool 510 has a wheel assembly 512 which includes readout dial 514 with performance setting indicia, metal yoke 516, first crown gear 522 fixed to an upper surface of yoke 516, magnets 518 and 520 mounted on a lower surface of yoke 516, all rotatable on bearing 517 mounted on platform 524 of indicator housing lower portion 534. Release button 530 has an enlarged head 531 at a lower end and has a second crown gear 532, serving as a catch when button 530 is in a first position, mounted by press fit at a middle axle section of button 530. An upper end of button 530 has a narrowed key element 533 which is movable vertically within slot 537 defined by indicator housing upper portion 538. Rotation of button 530 is prevented by the interaction of key element 533 with the side walls of slot 537. Bearing 517 enables translational, thrust movement of button 530 as well as enabling rotation of wheel assembly 512.

In this construction, the act of nesting indicator tool 510 into locator 500 causes a portion of head 531 of release button 530 to contact a portion of locator floor 504, near opening 502, which overcomes the downward bias provided by coil spring 540 to move button 530 from a first, normally locked position to a second, rotatable position as illustrated in FIG. 30. The act of removing indicator tool 510 from locator tool 500 allows spring 540 to automatically drive second, catch gear 532 downward to mesh with first gear 522 of wheel assembly 512. One of the performance setting indicia on dial 514 is then readable through magnifying lens 528 to record the actual setting of a valve unit.

Figure 31A:
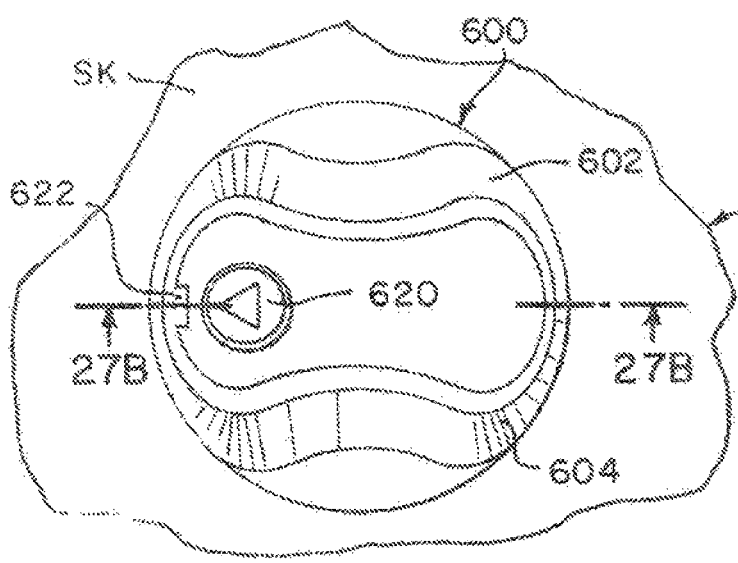
FIG. 31A is a top plan view of an adjuster tool positioned over a patient with the locator tool omitted.
Figure 31B:
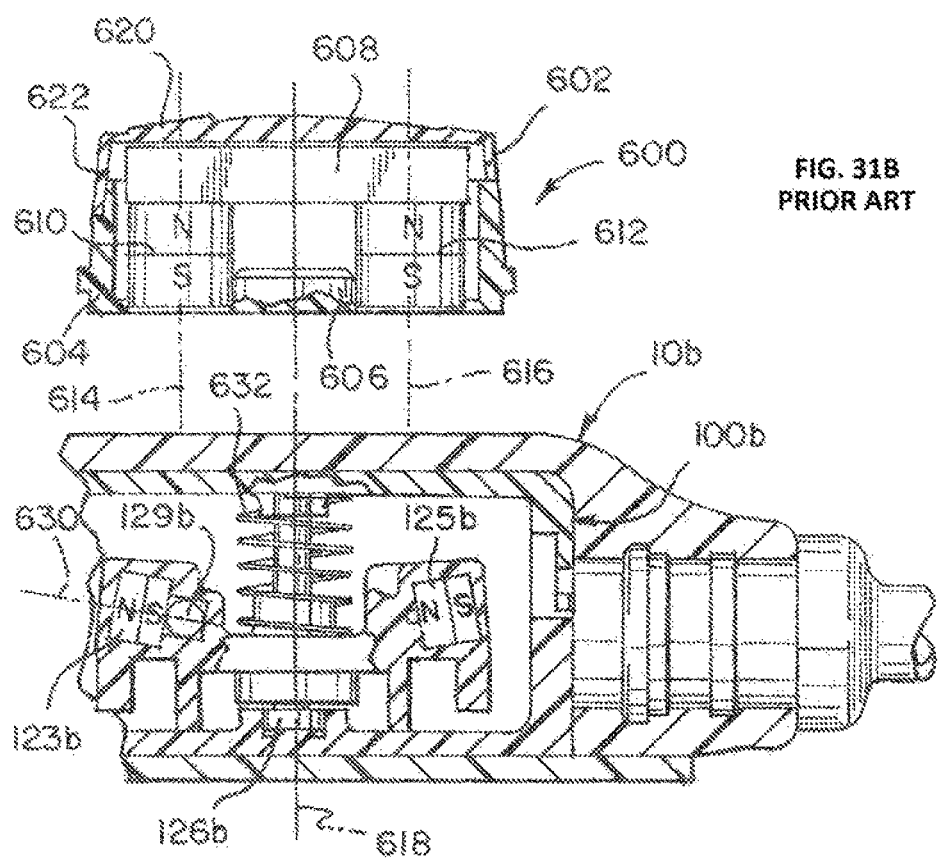
FIG. 31B is a schematic cross-sectional view along lines 27B-27B of FIG. 31A showing only the adjuster tool and a portion of the shunt valve with valve unit, shown at 10× scale.

An alternative adjuster tool 600 is shown in FIGS. 31A and 31B positioned over skin SK of a patient P with an implanted shunt valve 10b having a valve unit 100b, which is similar in construction to shunt valve 10a with valve unit 100a as shown and described above relative to FIG. 1. A locator tool as described above has been omitted from these drawings, and everything other than a portion of shunt valve 10b, at a scale of approximately 10× relative to adjuster tool 600, has been omitted from FIG. 31B for clarity in discussing orientation of magnetic polarities and axes of magnetization.

Adjuster tool 600 has an upper housing 602 and a lower housing 604 with an enlarged floor portion 606 to assist securing magnets 610 and 612 in position. Upper casing 602 has an integral directional arrow 620 for proper alignment with a locator tool and has a marker 622 which confirms directional alignment of upper casing 602 with lower casing 604 during assembly.

Adjuster magnets 610 and 612 are connected by metal yoke 608 and each has an axis of magnetization 614 and 616, respectively, which are substantially parallel in this construction as indicated with dashed lines. During adjustment of a valve unit such as valve unit 100b, axes of magnetization 614 and 616 are oriented to be substantially parallel to axis of rotation 618 through axle 126b of rotor 120b. In this construction, adjuster magnet 610 has a south pole S that is oriented to face rotor magnet 123b and imaging reference ball 129b while north pole N of magnet 612 is oriented to face rotor magnet 125b. Rotor 120b is shown in a constrained condition in FIG. 31B, and is lifted to an unconstrained condition when the lower surface of adjuster tool 600 approaches within three cm (less than 1.25 inches) of the floor of a locator tool positioned on skin SK, FIG. 31A.

Axis of magnetization 630 of rotor magnet 123*b* is shown having an angle 632 relative to axis of rotation 618, with north pole N facing radially outwardly relative to axis of rotation 618. Rotor magnet 125*b* has a similar axis of magnetization, but with south pole S facing radially outwardly away from axis of rotation 618. Angle 632 is approximately eighty degrees in this construction. While an angle of ninety degrees from axis of rotation 618 for the axes of magnetization for rotor magnets 123*b* and 125*b* may be most effective for detection of actual setting by an indicator tool, it has been found that offset angles of seventy-five to eighty-five degrees, most preferably approximately eighty degrees, are suitable for interaction with the adjustment tool 600. Further, having axes of magnetization other than zero degrees and ninety degrees reduces the likelihood of simultaneous de-magnetization of both rotor magnets when exposed to a magnetic field greater than 3 Tesla or other large electromagnetic field. In other words, it is preferable for the axes of magnetization of the rotor magnets to be offset relative to each other instead of parallel to each other to resist de-magnetization as well as to encourage binding of axle 126*b* when exposed to unintended magnetic fields.

Heretofore, a programmable valve has been designed expressly to operate only with its intended corresponding toolset. For the first time, the present inventive programmable valve in FIG. 1 has been expressly designed to take into consideration, at times, competing or counterintuitive conditions to ensure proper performance not just of the toolset expressly intended for use with the valve, but also remain compatible with toolsets not intended for use with the valve. In particular, the present inventive programmable valve in FIG. 1 has expressly been designed to be compatible not simply with its intended associated toolset, FIGS. 14-17, capable of individually discriminating each magnet (e.g., fixed reference magnet 800 and each of primary magnetic elements 123, 125) using sensor array 1570, but also with a toolset (for example, FIGS. 18-31) that is incapable of individually differentiating among the magnets because it utilizes an analog type compass, as described above. Thus resulting, at times, in competing criteria at play when designing the strength and placement of the fixed reference magnet 800 in the valve 10.

Due to these at times competing interests, intuitively, when designing a valve intended to be compatible with a toolset using an analog compass one would be inclined to use a radiopaque marker, rather than a magnet. The present inventive valve design intentionally employs instead a fixed reference magnet serving a dual purpose: (i) to ascertain the direction of flow or orientation of the valve when using an intended toolset including a sensor array; and, also (ii) with the non-intended toolset using an analog compass, to provide a direction of flow marker identifiable via X-ray.

In summary, consideration is accorded when designing the indicator tool of the intended toolset to such factors as the size and spacing of the magnets (e.g., each of the primary magnets 123, 125 and the fixed reference magnet) and configuration of the sensor array. At the same time, the size and positioning of the fixed reference magnet in the valve is designed to have minimal, if any, negative impact on the non-intended toolset employing an analog compass dial. Because the analog compass has a north and south magnet intended to couple with the north and south magnet of the valve it is counterintuitive to include another magnet (e.g., fixed reference magnet) in the valve that could undesirably influence the attraction of the compass away from the valve's primary magnetic elements. Within the range of approximately 17.5 mm to approximately 20.75 mm distance separation between the center of the fixed reference magnet and the center of the valve has minimal, if any, negative impact on the non-intended toolset employing an analog compass dial.

On the one hand, consideration was given to the intended toolset (FIGS. 14-17) and the ability of sensor array 1570 of the indicator tool to properly locate and differentiate each magnet independently (e.g., fixed reference magnet 800, each primary magnetic element 123, 125). Placement of fixed reference magnet 800 too close in relation to either of the primary magnetic elements 123, 125 or selecting a fixed reference magnet that is too strong would make differentiating the fixed reference magnet independent from each of the primary magnetic elements using the sensor array more difficult. Whereas, if the strength of the fixed reference magnet 800 chosen is too small the sensor array may be unable to detect its magnetic field, while placement of the fixed reference magnet further away from the primary magnetic elements introduces measurement error due to anatomical variability and would require a sensor array having a larger footprint (unwieldly to operate and increased cost to manufacture). Preferably, the center of the fixed reference magnet is offset from that of the center of the rotating construct by a range of approximately 17.5 mm to approximately 20.75 mm. In general, the fixed reference magnet is located beyond or outside a range of influence on the analog type compass assembly.

On the other hand, it is counterintuitive that a programmable valve that includes a fixed reference magnet, in addition to the primary magnetic elements 123, 125 may be properly operated using a non-intended toolset unable to individually differentiate among the magnets (e.g., employing an analog type compass mechanism, instead of a sensor array). Referring to FIG. 15, as discussed in detail above, the analog type compass configuration therein employs one or more freely rotating magnets (FIG. 15: 360, 362) that align with a resultant magnetic field produced by the primary magnets (123, 125) associated with the adjustable valve unit 100. When the indicator tool 302 is positioned with locator tool 304 over an implanted valve unit, such as shown in FIGS. 22-24, after button 322 is depressed, pressure wheel assembly 359 (including magnets 360, 362) (FIG. 15) rotates freely like an analog type compass until a north-south polarity is encountered corresponding to that of the primary magnets associated with the adjustable valve unit wherein the north-south polarity is stronger than the earth's magnetic field. The pressure wheel assembly 359 in the analog type compass configuration is unable to differentiate each primary magnet 123, 125 individually. Nor is the pressure wheel assembly 359 in indicator tool 302 of FIG. 15 able to independently detect fixed reference magnet 800. It is noted that since the toolset employing an analog type compass configuration is unable to independently detect the fixed reference magnet, orientation of the direction of flow of the implanted valve must be ascertained through other means, such as through palpation, using conventional methods. It stands to reason that the analog type compass configuration of the indicator tool 302 would be negatively influenced or skewed by the fixed reference magnet 800 resulting in improper alignment of the magnets 360, 362 of the indicator tool 302 with the primary magnets 123, 125 of the programmable valve resulting in an inaccurate setting indication and/or change in new setting having deleterious consequences to the health of the patient. One would logically conclude that the further the distance between the fixed reference magnet and the primary magnetic elements 123, 125 the less influence or skew on the analog type compass configuration and improved performance. Experimental testing was conducted using a toolset employing an analog compass type configuration (FIG. 19) in which the center of the fixed reference magnet was placed at different locations (e.g., 12 mm, 15 mm, 17.5 mm, 20.75 mm) from the center of the rotating construct 120 (i.e., the center of the adjustable valve unit 100). As expected there is a threshold for how close the fixed reference magnet can be prior to negatively influencing the analog indicator. Counterintuitively, testing results have verified that there is a distance (17.5 mm or 20.75 mm) that fits within the profile of the implanted valve that does not negatively interact with the analog compass.

Yet another significant advantage to having compatibility of a valve with three magnetic elements (e.g., pair of primary magnetic elements 123, 125 and a fixed reference magnet 800) with a non-intended toolset employing an analog compass is that manufacture of the valve may be streamlined to a single configuration (employing three magnetic elements), rather than have to maintain manufacture of a valve that differs in the number of magnets (i.e., manufacture one valve with two magnets for one toolset and manufacture a different valve having three magnets for another electronic toolset). Not only is such streamlining advantageous from a cost perspective, but also, fosters customer satisfaction if users preferring one toolset over the other can maintain use thereof. Thus, less disruption is incurred by entrenched customers while providing continual improvement to the platform.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A method for using an implantable programmable bodily fluid drainage valve including a fixed reference magnet and an adjustable valve unit having a pair of primary magnetic elements, the method comprising the steps of:
    operating the implantable programmable bodily fluid drainage valve that is operable by both a first toolset including a sensor array for detecting a magnetic field and a second toolset employing an analog type compass assembly instead of the sensor array; wherein when operating the implantable programmable bodily fluid drainage valve using the second toolset, a location of the fixed reference magnet in the implantable programmable bodily fluid drainage valve and size of the fixed reference magnet has substantially no negative influence on operation of the analog type compass assembly of the second toolset.

2. The method in accordance with claim 1, wherein the sensor array detects independently the fixed reference magnet and each of the pair of primary magnetic elements.

3. The method in accordance with claim 1, wherein when operating the implantable programmable bodily fluid drainage valve using the second toolset, the analog type compass assembly has a north-south polarity freely rotatable like a compass until coupled with a north-south polarity of the primary magnetic elements of the adjustable valve unit to properly indicate a current setting of the valve.

4. The method in accordance with claim 1, wherein the pair of primary magnetic elements are housed in a rotating construct; and the fixed reference magnet is located beyond a range of influence on the analog type compass assembly when operating the implantable programmable bodily fluid drainage valve using the second toolset.

5. The method in accordance with claim 4, wherein a distance separation between a center of the fixed reference magnet and a center of the adjustable valve is within a range approximately 17.5 mm to approximately 20.75 mm so that the fixed reference magnet is outside the range of influence on the analog type compass assembly when operating the implantable programmable bodily fluid drainage valve using the second toolset.

* * * * *